US005783683A

United States Patent [19]
Morrison

[11] Patent Number: 5,783,683
[45] Date of Patent: Jul. 21, 1998

[54] ANTISENSE OLIGONUCLEOTIDES WHICH REDUCE EXPRESSION OF THE FGFRI GENE

[75] Inventor: Richard S. Morrison, Redmond, Wash.

[73] Assignee: Genta Inc., San Diego, Calif.

[21] Appl. No.: 371,001

[22] Filed: Jan. 10, 1995

[51] Int. Cl.$^6$ .......................... C07H 21/04; C07H 21/02; C12N 15/00

[52] U.S. Cl. .......................... 536/24.5; 536/23.1; 514/44; 435/172.3

[58] Field of Search .................... 536/22.1, 23.1, 536/24.1, 24.5; 435/320.1, 91.1; 424/95.1; 514/44, 2

[56] References Cited

U.S. PATENT DOCUMENTS 5,459,015  10/1995  Janjic et al. .................... 435/6

FOREIGN PATENT DOCUMENTS

WO 94/15945  7/1994  WIPO.
9500528  1/1995  WIPO.

OTHER PUBLICATIONS

Orkin et al. Report and Recommendations of the panel to assess the NIH investment in research on gene therapy. Distributed by the National Institutes of Health, Dec. 7, 1995.
Morrison et al., Cancer Res., 50, 1990, 2524–2529.
Porcu et al., Mol. And Cell. Biol., 12(11), 1992, 5069–5077.
Redekop et al., J. Neurosurgery, 82, 1995, 83–90.
Stein et al., Science, 261, 1993, 1004–1012.
Morishita et al., J. Cell. Biochem. Supp. 0, 17 part E, 1993, 239.
Noble et al., J. Cell. Biochem. Supp. 0, 17 part E, 1993, 219.
Morrison, J. Biol. Chem., 266(2), 1991, 728–734.

Primary Examiner—Jasemine C. Chambers
Assistant Examiner—Deborah J. R. Clark
Attorney, Agent, or Firm—Knobbe Martens Olson & Bear LLP

[57] ABSTRACT

Antisense molecules, compositions thereof, and vectors encoding antisense RNA, and methods of using antisense molecules, compositions, and vectors for treating human glioblastoma cells in order to suppress the growth of the cells. The antisense molecules are substantially complementary to human fibroblast growth factor receptor gene one (the FGFR1).

6 Claims, 9 Drawing Sheets

Influence of FGFR1 Antisense Oligonucleotides on the Growth of T98 Human Glioblastoma Cells In Vitro The addition of 30 μM FGFR1 α exon antisense oligonucleotide resulted in a 34% reduction in cell number. No effect was observed with the control antisense oligonucleotide.

Influence of FGFR1 Antisense Oligonucleotides on the Growth of T98 Human Glioblastoma Cells In Vitro The addition of 30 μM FGFR1 α exon antisense oligonucleotide resulted in a 34% reduction in cell number. No effect was observed with the control antisense oligonucleotide.

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: Other Nucleic Acid ( x i ) SEQUENCE DESCRIPTION: SEQ ID NO:1:

CTGCACATCG TCCCGCAGCC                                                    20

( 2 ) INFORMATION FOR SEQ ID NO:2:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: Other Nucleic Acid ( x i ) SEQUENCE DESCRIPTION: SEQ ID NO:2:

CGAGCTCACT GTGGAGTATC CATG                                               24

( 2 ) INFORMATION FOR SEQ ID NO:3:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: Other Nucleic Acid ( x i ) SEQUENCE DESCRIPTION: SEQ ID NO:3:

GTTACCCGCC AAGCACGTAT AC                                                 22

( 2 ) INFORMATION FOR SEQ ID NO:4:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: Other Nucleic Acid ( x i ) SEQUENCE DESCRIPTION: SEQ ID NO:4:

AAGTGTGCAG ATGGGATTAA CGTC                                               24

( 2 ) INFORMATION FOR SEQ ID NO:5:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: Other Nucleic Acid ( x i ) SEQUENCE DESCRIPTION: SEQ ID NO:5:

ATTACCCGCC AAGCACGTAT AT                                                 22

( 2 ) INFORMATION FOR SEQ ID NO:6:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Other Nucleic Acid ( x i ) SEQUENCE DESCRIPTION: SEQ ID NO:6:

ACGGATTTGG TCGTATTGGG                                                    20

( 2 ) INFORMATION FOR SEQ ID NO:7:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: Other Nucleic Acid ( x i ) SEQUENCE DESCRIPTION: SEQ ID NO:7:

TGATTTTGGA GGGATCTCGC                                                                       20

( 2 ) INFORMATION FOR SEQ ID NO:8:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: Other Nucleic Acid ( x i ) SEQUENCE DESCRIPTION: SEQ ID NO:8:

ATAACGGACC TTGTAGCCTC C                                                    21

( 2 ) INFORMATION FOR SEQ ID NO:9:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: Other Nucleic Acid ( x i ) SEQUENCE DESCRIPTION: SEQ ID NO:9:

GGTCGTTTCA TCTGCCTGGT C                                                   21

( 2 ) INFORMATION FOR SEQ ID NO:10:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: Other Nucleic Acid ( x i ) SEQUENCE DESCRIPTION: SEQ ID NO:10:

CCGACGCCCT GCTACACGTC                                                         20

( 2 ) INFORMATION FOR SEQ ID NO:11:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: Other Nucleic Acid ( x i ) SEQUENCE DESCRIPTION: SEQ ID NO:11:

CGTCTTGACC CTACACCTCG                                                         20

( 2 ) INFORMATION FOR SEQ ID NO:12:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: Other Nucleic Acid ( x i ) SEQUENCE DESCRIPTION: SEQ ID NO:12:

GGCATTGGTA CCAGTCGACC C   21

( 2 ) INFORMATION FOR SEQ ID NO:13:

( i ) SEQUENCE CHARACTERISTICS:
       ( A ) LENGTH: 20 base pairs
       ( B ) TYPE: nucleic acid
       ( C ) STRANDEDNESS: single
       ( D ) TOPOLOGY: linear ( i i ) MOLECULE TYPE: Other Nucleic Acid ( x i ) SEQUENCE DESCRIPTION: SEQ ID NO:13:

GCTCCACATC CCAGTTCTGC   20

( 2 ) INFORMATION FOR SEQ ID NO:14:

( i ) SEQUENCE CHARACTERISTICS:
       ( A ) LENGTH: 2733 base pairs
       ( B ) TYPE: nucleic acid
       ( C ) STRANDEDNESS: single
       ( D ) TOPOLOGY: linear ( i i ) MOLECULE TYPE: DNA (genomic)

( i x ) FEATURE:
       ( A ) NAME/KEY: misc_feature
       ( B ) LOCATION: 210..467
       ( D ) OTHER INFORMATION: FGFR1 Alpha Exon ( i x ) FEATURE:
       ( A ) NAME/KEY: misc_feature
       ( B ) LOCATION: 57
       ( D ) OTHER INFORMATION: "IDENTITY OF
          NUCLEOTIDE PROVISIONAL"

( i x ) FEATURE:
       ( A ) NAME/KEY: misc_feature
       ( B ) LOCATION: 117
       ( D ) OTHER INFORMATION: "IDENTITY OF
          NUCLEOTIDE PROVISIONAL"

( x i ) SEQUENCE DESCRIPTION: SEQ ID NO:14:

| | | | | | |
|---|---|---|---|---|---|
| CGAGGCGGAA | CCTCCAGCCC | GAGCGAGGGT | CAGTTTGAAA | AGGAGGATCG | AGCTCANCTG   60 |
| TGGAGTATCC | ATGGAGATGT | GGAGCCTTGT | CACCAACCTC | TAACTGCAGA | ACTGGGNATG  120 |
| TGGAGCTGGA | AGTGCCTCCT | CTTCTGGGCT | GTGCTGGTCA | CAGCCACACT | CTGCACCGCT  180 |
| AGGCCGTCCC | CGACCTTGCC | TGAACAAGCC | CAGCCCTGGG | GAGCCCCTGT | GGAAGTGGAG  240 |
| TCCTTCCTGG | TCCACCCCGG | TGACCTGCTG | CAGCTTCGCT | GTCGGCTGCG | GGACGATGTG  300 |
| CAGAGCATCA | ACTGGCTGCG | GGACGGGGTG | CAGCTGGCGG | AAAGCAACCG | CACCCGCATC  360 |
| ACAGGGGAGG | AGGTGGAGGT | GCAGGACTCC | GTGCCCGCAG | ACTCCGGCCT | CTATGCTTGC  420 |
| GTAACCAGCA | GCCCCTCGGG | CAGTGACACC | ACCTACTTCT | CCGTCAATGT | TTCAGATGCT  480 |
| CTCCCCTCCT | CGGAGGATGA | TGATGATGAT | GATGACTCCT | CTTCAGAGGA | GAAAGAAACA  540 |
| GATAACACCA | AACCAAACCG | TATGCCCGTA | GCTCCATATT | GGACATCCCC | AGAAAAGATG  600 |
| GAAAAGAAAT | TGCATGCAGT | GCCGGCTGCC | AAGACAGTGA | AGTTCAAATG | CCCTTCCAGT  660 |
| GGGACCCCAA | ACCCCACACT | GCGCTGGTTG | AAAAATGGCA | AGAATTCAA | ACCTGACCAC  720 |
| AGAATTGGAG | GCTACAAGGT | CCGTTATGCC | ACCTGGAGCA | TCATAATGGA | CTCTGTGGTG  780 |
| CCCTCTGACA | AGGGCAACTA | CACCTGCATT | GTGGAGAATG | AGTACGGCAG | CATCAACCAC  840 |

| | | | | | |
|---|---|---|---|---|---|
| ACATACCAGC | TGGATGTCGT | GGAGCGGTCC | CCTCACCGGC | CCATCCTGCA | AGCAGGGTTG | 900
| CCCGCCAACA | AAACAGTGGC | CCTGGGTAGC | AACGTGGAGT | TCATGTGTAA | GGTGTACAGT | 960
| GACCCGCAGC | CGCACATCCA | GTGGCTAAAG | CACATCGAGG | TGAATGGGAG | CAAGATTGGC | 1020
| CCAGACAACC | TGCCTTATGT | CCAGATCTTG | AAGACTGCTG | GAGTTAATAC | CACCGACAAA | 1080
| GAGATGGAGG | TGCTTCACTT | AAGAAATGTC | TCCTTTGAGG | ACGCAGGGGA | GTATACGTGC | 1140
| TTGGCGGGTA | ACTCTATCGG | ACTCTCCCAT | CACTCTGCAT | GGTTGACCGT | TCTGGAAGCC | 1200
| CTGGAAGAGA | GGCCGGCAGT | GATGACCTCG | CCCTGTACC | TGGAGATCAT | CATCTATTGC | 1260
| ACAGGGGCCT | TCCTCATCTC | CTGCATGGTG | GGGTCGGTCA | TCGTCTACAA | GATGAAGAGT | 1320
| GGTACCAAGA | AGAGTGACTT | CCACAGCCAG | ATGGCTGTGC | ACAAGCTGGC | CAAGAGCATC | 1380
| CCTCTGCGCA | GACAGGTAAC | AGTGTCTGCT | GACTCCAGTG | CATCCATGAA | CTCTGGGGTT | 1440
| CTTCTGGTTC | GGCCATCACG | GCTCTCCTCC | AGTGGGACTC | CCATGCTAGC | AGGGGTCTCT | 1500
| GAGTATGAGC | TTCCCGAAGA | CCCTCGCTGG | GAGCTGCCCT | CGGGACAGAC | TGGTCTTAGG | 1560
| CAAACCCCTG | GGAGAGGGCT | GCTTTGGGCA | GGTGGTGTTG | GCAGAGGCTA | TCGGGCTGGA | 1620
| CAAGGACAAA | CCCAACCGTG | TGACCAAAGT | GGCTGTGAAG | ATGTTGAAGT | CGGACGCAAC | 1680
| AGAGAAAGAC | TTGTCAGACC | TGATCTCAGA | AATGGAGATG | ATGAAGATGA | TCGGGAAGCA | 1740
| TAAGAATATC | ATCAACCTGC | TGGGGGCCTG | CACGCAGGAT | GGTCCCTTGT | ATGTCATCGT | 1800
| GGAGTAGCCT | CCAAGGGCAA | CCTGCGGGAG | TACCTGCAGG | CCCGGAGGCC | CCCAGGGCTG | 1860
| GAATACTGCT | ACAACCCCAG | CCACAACCCA | GAGGAGCAGC | TCTCCTCCAA | GGACCTGGTG | 1920
| TCCTGCGCCT | ACCAGGTGGC | CCGAGGCATG | GAGTATCTGG | CCTCCAAGAA | GTGCATACAC | 1980
| CGAGACCTGG | CAGCCAGGAA | TGTCCTGGTG | ACAGAGGACA | ATGTGATGAA | GATAGCAGAC | 2040
| TTTGGCCTCG | CACGGGACAT | TCACCACATC | GACTACTATA | AAAAGACAAC | CAACGGCCGA | 2100
| CTGCCTGTGA | AGTGGATGGC | ACCCGAGGCA | TTATTTGACC | GGATCTACAC | CCACCAGAGT | 2160
| GATGTGTGGT | CTTTCGGGGT | GCTCCTGTGG | GAGATCTTCA | CTCTGGGCGG | CTCCCCATAC | 2220
| CCCGGTGTGC | CTGTGGAGGA | ACTTTTCAAG | CTGCTGAAGG | AGGGTCACCG | CATGGACAAG | 2280
| CCCAGTAACT | GCACCAACGA | GCTGTACATG | ATGATGCGGG | ACTGCTGGCA | TGCAGTGCCC | 2340
| TCACAGAGAC | CCACCTTCAA | GCAGCTGGTG | GAAGACCTGG | ACCGCATCGT | GGCCTTGACC | 2400
| TCCAACCAGG | AGTACCTGGA | CCTGTCCATG | CCCCTGGACC | AGTACTCCCC | CAGCTTTCCC | 2460
| GACACCCGGA | GCTCTACGTG | CTCCTCAGGG | GAGGATTCCG | TCTTCTCTCA | TGAGCCGCTG | 2520
| CCCGAGGAGC | CCTGCCTGCC | CCGACACCCA | GCCCAGCTTG | CCAATCGGGG | ACTCAAACGC | 2580
| CGCTGACTGC | CACCCACACG | CCCTCCCCAG | ACTCCACCGT | CAGCTGTAAC | CCTCACCCAC | 2640
| AGCCCCTGCT | GGGCCCACCA | CCTGTCCGTC | CCTGTCCCCT | TTCCTGCTGG | CAGCCGGCTG | 2700
| CCTACCAGGG | GCCTTCCTGT | GTGGCCTGCT | TCA | | | 2733

ANTISENSE OLIGONUCLEOTIDES WHICH REDUCE EXPRESSION OF THE FGFRI GENE

BACKGROUND OF THE INVENTION

1. Field of the Invention

This invention relates to antisense molecules for suppressing the growth of tumor cells, and to methods for using the antisense molecules to suppress the growth of tumor cells. In particular, the invention is directed to compositions of antisense oligonucleotides and methods for suppressing the growth of glioblastoma cells.

2. Description of Related Art

The publications and other reference materials referred to herein to describe the background of the invention and to provide additional detail regarding its practice are hereby incorporated by reference. For convenience, the reference materials are numerically referenced and grouped in the appended bibliography.

The vast majority of primary central nervous system tumors in humans are glial cell-derived neoplasms (gliomas or glioblastomas). Most of these neoplasms derive from the astrocyte line of brain cells.

Routine forms of cancer therapy, such as surgery, radiation therapy and chemotherapy are either not effective against human glioblastomas or are not specific for glioblastoma cells. As a result, the average survival time for a patient with glioblastoma multiforme is approximately 14 months.

The vast majority (90%) of human glioblastomas are resistant to traditional chemotherapeutic agents, such as the commonly used alkylating agents.

Furthermore, these agents are not specific for cancer cells and inhibit the growth of any cell that is proliferating. As a result, these agents have many side effects. The same limitations apply to radiation therapy. There is presently no form of immunotherapy or gene therapy that is effective against human glioblastomas.

Although the causes of astrocytic tumors remains obscure, the transformation of normal cells into cancerous ones and their progression into malignancy has been partially characterized at the biochemical level. It has been found that many malignant tissues produce an abnormally large amount of basic fibroblast growth factor (BFGF), a protein which stimulates cells to divide and grow (1,2,3).

It is believed that the effects of BFGF are mediated through specific binding with fibroblast growth factor receptor proteins (FGFRs). FGFRs are membrane bound proteins. Four structurally related genes encoding five high-affinity FGFRs have been identified (4–9). FGF proteins and receptors have been identified in human glioma cells (10), however, their role in glioblastoma growth and invasion of normal tissues is not understood.

Antisense oligodeoxynucleotides are one example of a specific therapeutic tool with the potential for ablating oncogene function. These short (usually about 30 bases) single-stranded synthetic oligonucleotides have a base sequence complementary to the target pre-mRNA (heterogeneous nuclear RNA—hnRNA) or mRNA and form a hybrid duplex by hydrogen bonded base pairing. The targeted RNA duplexed by forms of antisense oligonucleotide such as diesters, phosphorthioates, or phosphorodithioates is subject to RNaseH degradation in the duplexed region. Antisense oligonucleotides generally work by a cleavage mode of action [??] or sterically blocking enzymes involved in processing pre-mRNA or translation of mRNA. This hybridization can be expected to prevent expression, i.e. translation of the target mRNA code into its protein product and thus preclude subsequent effects of the protein product. Because the mRNA sequence expressed by the gene is termed the sense sequence, the complementary sequence is termed the antisense sequence. Under some circumstances, degradation of mRNA would be more efficient than inhibition of an enzyme's active site, since one mRNA molecule gives rise to multiple protein copies.

Synthetic oligodeoxynucleotides have been used to specifically inhibit production of c-myc protein, thus arresting the growth of human leukemic cells in vitro (11). Oligodeoxynucleotides have also been employed as specific inhibitors of retroviruses, including the human immunodeficiency virus (HIV-I) (12). Attempts have been made using oligodeoxynucleotides to suppress bFGF expression, and inhibit growth of transformed human astrocytes in culture (13,14). The mechanism of action by which these oligonucleotides achieve their effects is a matter of controversy.

Accordingly, further developments are needed to develop a therapy that is specific for human glioblastoma tumors and which suppresses, inhibits, prevents or significantly reduces the growth of human glioblastoma cells as a means of curing, or at least improving the survival and morbidity associated with the occurrence of glioblastoma multiforme tumors in humans.

SUMMARY OF THE INVENTION

The claimed invention overcomes the above-mentioned problems, and provides antisense molecules, compositions of antisense molecules and a method of using the claimed molecules and compositions which provide the advantage of inhibiting, preventing, or significantly reducing the growth of human glioblastoma cells as a means of curing, or at least improving the survival and morbidity associated with the occurrence of glioblastoma multiforme tumors in humans.

The invention is based upon the discovery that contacting glioblastoma cells with the claimed antisense molecules, which have a sequence substantially complementary to FGFR1$\alpha$, reduces the appearance of all forms of FGFR1, including FGFR1$\beta$, and thereby suppresses the growth of the glioblastoma cells.

The claimed antisense oligomers bind to a sequence portion of RNA expressed from the human FGFR1gene, the $\alpha$ exon, which encodes the first immunoglobulin-like domain. When brought into contact with tumor cells expressing the human FGFR1 gene, the claimed antisense molecules selectively reduce the expression of at least one FGFR1 gene product, thereby suppressing the growth of the tumor cells.

The invention further includes compositions of the claimed antisense molecules together with a pharmaceutically acceptable carrier.

Another feature of the invention provides vectors for transfecting human tumor cells. The claimed vectors comprise a nucleotide sequence that encodes an antisense RNA which reduces expression from the human FGFR1 gene in tumor cells, and which has the property of reducing the expression of at least one FGFR1 gene product, thereby suppressing the growth of the tumor cells.

A method is provided in the invention for suppressing the growth of tumor cells. The method comprises the step of introducing the claimed antisense oligomers and compositions thereof to tumor cells expressing the FGFR1. The conditions under which the claimed method introduces the antisense molecules to the tumor cells are sufficient to reduce FGFR1 gene expression in the tumor cells, and suppress the growth of the tumor cells.

The above discussed and many other features and attendant advantages of the present invention will become better understood by reference to the following detailed description of the invention when taken in conjunction with the accompanying drawings.

DETAILED DESCRIPTION OF THE INVENTION

Figure 1:
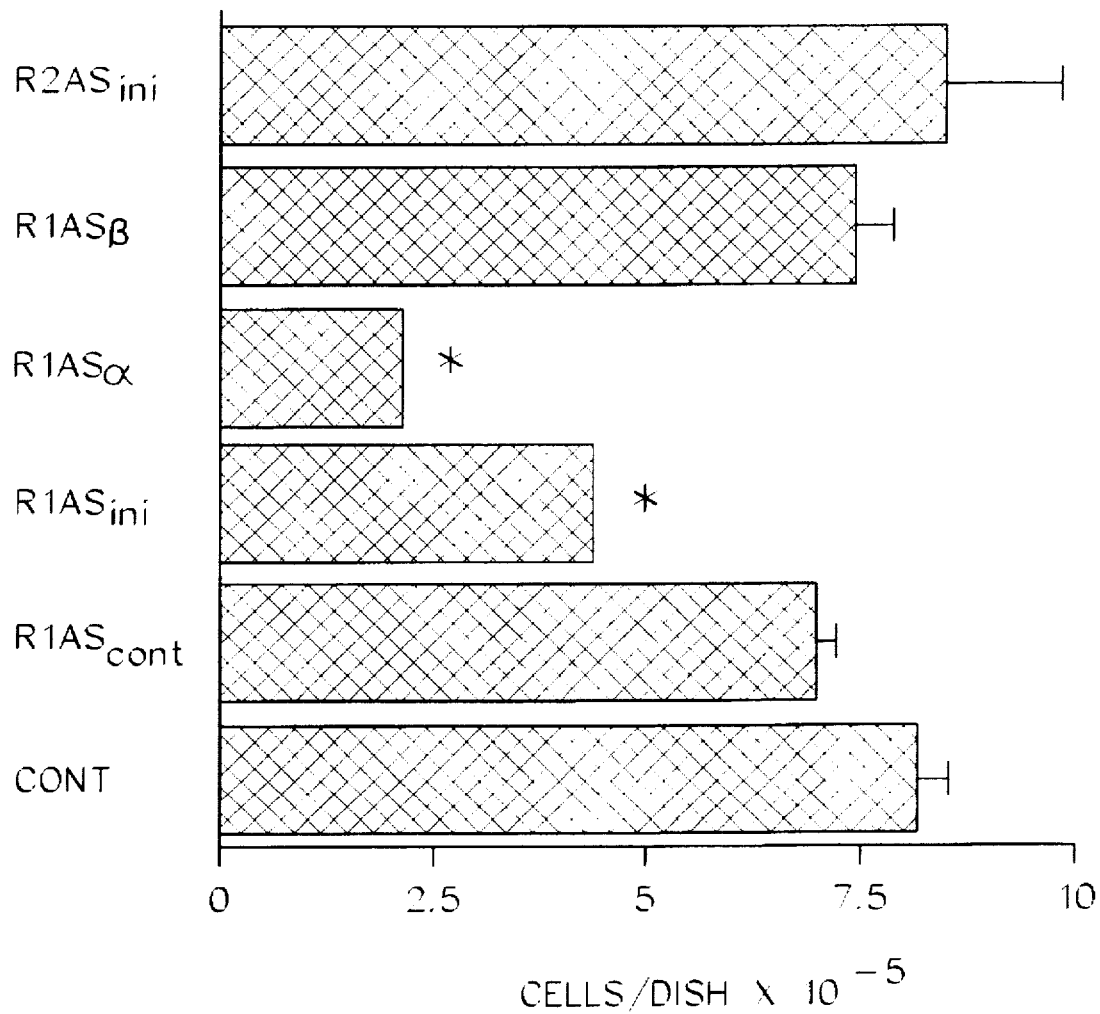
FIG. 1 shows the influence of claimed antisense and control oligomers on glioblastoma cell growth.

According to the invention, antisense oligomers and compositions thereof are provided for inhibiting the growth of glioblastoma cells. The invention also provides vectors comprising nucleotide sequences that encode the antisense oligomers of the invention. Also included in the invention are methods for inhibiting the growth of glioblastomas in humans which involve a step of introducing the claimed antisense oligomers to human glioblastoma cells.

Definitions

As used herein, the term "antisense oligomer" means antisense oligonucleotides and analogs thereof and refers to a range of chemical species having a range of nucleotide base sequences that recognize polynucleotide target sequences or sequence portions through hydrogen bonding interactions with the nucleotide bases of the target sequences. The target sequences may be single- or double-stranded RNA, or single- or double-stranded DNA.

The antisense oligonucleotides and analogs thereof may be RNA or DNA, or analogs of RNA or DNA, commonly referred to as antisense oligomers or antisense oligonucleotides. Such RNA or DNA analogs comprise but are not limited to 2'-O-alkyl sugar modifications, methylphosphonate, phosphorothioate, phosphorodithioate, formacetal, 3'-thioformacetal, sulfone, sulfamate, and nitroxide backbone modifications, amides, and analogs wherein the base moieties have been modified. In addition, analogs of oligomers may be polymers in which the sugar moiety has been modified or replaced by another suitable moiety, resulting in polymers which include, but are not limited to, morpholino analogs and peptide nucleic acid (PNA) analogs (51). Such analogs include various combinations of the above-mentioned modifications involving linkage groups and/or structural modifications of the sugar or base for the purpose of improving RNAseH-mediated destruction of the targeted RNA, binding affinity, nuclease resistance, and or target specificity.

Antisense analogs may also be mixtures of any of the oligonucleotide analog types together or in combination with native DNA or RNA. At the same time, the oligonucleotides and analogs thereof may be used alone or in combination with one or more additional oligonucleotides or analogs thereof. The oligonucleotides may be from about 10 to about 100 nucleotides long. Although oligonucleotides of 10 to 30 nucleotides are useful in the invention, preferred oligonucleotides range from about 15 to about 24 bases in length.

Antisense oligonucleotides and analogs thereof also comprise conjugates of the oligonucleotides and analogs thereof (16). Such conjugates have properties which improve the uptake, pharmacokinetics, and nuclease resistance of the oligonucleotide, or the ability to enhance cross-linking or cleavage of the target sequence by the oligonucleotide.

As used herein, the term "cell proliferation" refers to cell division. The term "growth," as used herein, encompasses both increased cell numbers due to faster cell division and due to slower rates of apoptosis, i.e. cell death.

Uncontrolled cell proliferation is a marker for a cancerous or abnormal cell type. Normal, non-cancerous cells divide regularly, at a frequency characteristic for the particular type of cell. When a cell has been transformed into a cancerous state, the cell divides and proliferates uncontrollably. Inhibition of proliferation or growth modulates the uncontrolled division of the cell.

"Antisense therapy" as used herein is a generic term which includes the use of specific binding oligomers to inactivate undesirable DNA or RNA sequences in vitro or in vivo using either triplex strand or antisense approaches.

As used herein, FGFR1α exon refers either to the complete nucleotide sequence of the FGFR1α exon as set forth in SEQUENCE ID NO. 14, or to a sequence portion of the FGFR1α exon. Sequence portions comprising the FGFR1α exon refer herein to at least a portion of the FGFR1α exon.

FGFR Gene Expression

As used herein, FGFR gene expression refers to RNA expression from a human FGFR gene, or to FGFR protein production from a human FGFR gene. Four structurally related genes encoding high affinity FGF receptors (FGFR) have been identified (4–8).

In addition to high-affinity binding sites, cells exhibit low-affinity FGF binding sites (17) which have been characterized as either cell-associated or extra-cellular heparan sulfate proteoglycans (18,19). Binding to the low-affinity, glycosaminoglycan sites appears to be obligatory for FGF binding to high affinity receptors and for biological activity (20,21). Cells deficient in heparan sulfate biosynthesis are not able to bind or respond to bFGF (31–32). However, the addition of either free heparan or heparan sulfate restores high-affinity binding of bFGF (20). These results demonstrate that heparin-like, low-affinity sites play an important role in the regulation of bFGF activity and in the response of cells to bFGF.

FGFR Gene Structures

Structural features common to members of the FGFR family include a signal peptide, two or three immunoglobulin-like loops in the extracellular domain, a hydrophobic transmembrane domain and a highly conserved tyrosine kinase domain split by a short kinase insert sequence (22). Overall, the proteins encoded by the four FGFR genes are strikingly similar. The most closely related proteins are FGFR1 and FGFR2 (72% amino acid identity), whereas FGFR1 and FGFR4 are the least closely related (55% identity). Each of the FGFR's can bind several different types of FGF'S. However, there are several reports of cell- and tissue-specific expression of FGF receptors and responsiveness to different FGF family members (23,24,25).

One mechanism for generating this selective responsiveness to different FGF family members would be to alter the ligand binding specificity or affinity through alternative splicing of RNA, thereby producing several receptor isoforms from a single gene.

FGFR Structural Variants

Structural variants of FGFR1, FGFR2 and FGFR3 are, in fact, generated by alternative splicing of their RNA transcripts (22). The divergent receptors generated by this process manifest different ligand-binding specificities and affinities (22).

One common structural variation that involves the second half of the third immunoglobulin (Ig)-like disulfide loop of FGFR1 and FGFR2 dramatically alters these receptors' ligand-binding properties (26). Another splicing variant results in FGFRs containing either two or three Ig-like domains in the extracellular region (5,27,28). Alternative RNA splicing involving both the first and third Ig-like domains is subject to cell- and tissue-specific processing that reflect the changing FGF requirement that occurs during tissue growth and differentiation (5,24)

The FGFR's appear to be differentially expressed in diverse tissue types and during different periods of development. Studies that have examined the distribution of FGFR's have relied principally on Northern blotting, the RNase protection assay and in situ hybridization to demonstrate the presence of mRNA transcripts. In general, FGFR1 and FGFR2 appear to be broadly distributed, while FGFR3 and FGFR4 exhibit more restricted patterns of distribution. For example, in the developing embryo FGFR1 transcripts are predominant in the central nervous system and in mesenchyme. FGFR2 transcripts are also observed in the central nervous system and in epithelium (25). FGFR3 transcripts are predominantly expressed in the central nervous system and cartilaginous rudiments of developing bone. In contrast to the other FGFR's, which are expressed to some degree in the central nervous system, FGFR4 transcripts are observed in developing endoderm, the myotomal compartment of somites and in myotomally-derived skeletal muscle. The unique temporal and spatial patterns of expression exhibited by different FGFR family members strongly suggest that they have distinct, but still unknown roles in tissue development, maintenance and pathology.

FGFR Expression and Transformation

In some types of human cancers, FGFR family members are amplified (31). Recent reports demonstrate a change in the expression of FGFRs during the course of a normal human tissue progressing to a malignant one (32,33). These reports demonstrate that in human glioblastomas differential expression and alternative splicing of FGFRs play a role in the transformation of normal cells and in malignant progression of astrocytic tumors. Normal astrocytes express the FGFR2 receptor and do not express the FGFR1 receptor. At the earliest stages of transformation, astrocytes begin to express FGFR1. Also at the earliest stage of transformation, FGFR1 is expressed in both the alpha and beta isoforms, although the alpha form generally predominates. As astrocytic tumors progress to the more malignant stages eventually culminating in a glioblastoma multiforme, their expression of FGFR1 shifts from the alpha form to almost exclusively the beta form. In addition to shifting to the beta form of FGFR1, the cells stop expressing FGFR2.

The Claimed Antisense Oligomers

The present invention is based upon the finding that antisense oligomers substantially complementary to and binding at least a portion of the alpha exon of the FGFR1 pre-mRNA or mRNA inhibited or reduced expression of all FGFR1 isoforms and resulted in growth suppression of glioblastoma cells. In particular, the present invention demonstrated that upon introducing the claimed antisense molecules to glioblastoma tumor cells, the growth of the tumor cells was suppressed, and that FGFR1 mRNA was selectively suppressed upon application of the claimed antisense molecules, as well as suppressing the expression of FGFR1α protein, and that further, FGFR1β, which is a major alternatively spliced form of FGFR1, was suppressed.

The present invention demonstrated that an FGFR1 antisense oligonucleotides complementary to the alpha exon were effective in reducing cell proliferation and reducing expression of FGFR1 mRNA. The present invention takes advantage of using antisense oligomers substantially complementary to and binding to at least a portion of the FGFR1 alpha exon pre-mRNA to suppress glioblastoma cells in which the major pre-mRNA or mRNA transcript encodes the beta isoform of FGFR1 protein. Nevertheless, FGFR1-alpha exon specific antisense oligonucleotide proved more effective in suppressing glioblastoma cell growth than the oligonucleotide complementary to the FGFR1 beta exon or complementary to the initiation site, although antisense oligomers directed to the translation initiation site proved effective in suppressing the growth of glioblastoma cells.

Antisense oligomers suitable for use in the invention include nucleotide oligomers which are preferably from about 10 to about 30 bases long, more preferably 12 to about 30 bases long, and most preferably 15 to 24 bases long. The oligonucleotides are preferably selected from those oligonucleotides substantially complementary to at least a portion of the FGFR1 alpha-exon or the translation start site. "Substantially complementary" as used herein means an antisense oligomers having about 80% homology with an antisense oligonucleotide which itself is complementary to and specifically binds to at least a sequence portion of the human FGFR1 alpha exon pre-mRNA. Degrading pre-mRNA or mature mRNA at the alpha-exon or at the translation start site prevents formation of a functional transcript, thereby blocking formation of the protein.

It should also be appreciated that antisense oligomers suitable for use in the invention may also include oligonucleotides which are directed to and substantially complementary to target sequences or sequence portions flanking either the alpha exon site or translation initiation site along the FGFR1 mRNA. The flanking sequence portions are preferably from about two to about twenty bases in length. It is also preferable that the antisense oligomers be substantially complementary to a sequence portion of the pre-mRNA or mRNA that is not commonly found in pre-mRNA or mRNA of other genes to minimize homology of antisense oligomers for pre-mRNA or mRNA coding strands from other genes.

The invention comprises an antisense or complementary oligomer comprising the sequence (SEQUENCE ID NO. 1)

5' CTG-CAC-ATC-GTC-CCG-CAG-CC 3'

As set forth in the Examples below, the claimed antisense oligomer disclosed in SEQ ID NO. 1 is substantially complementary to nucleotides numbered 284 to 303 in the FGFR1 gene sequence shown in SEQUENCE ID NO. 14. The FGFR1 alpha exon is 267 nucleotides long, and stretches from nucleotide number 210 to number 467 of SEQUENCE ID NO. 14. The claimed antisense oligomers when brought into contact with tumor cells expressing FGFR1 gene products (pre-mRNA and FGFR1 protein), reduce the expression of at least on FGFR1 gene product and inhibit the growth of those cells.

It will be appreciated by those skilled in the art to which this invention pertains that antisense oligomers having a greater or lesser number of substituent nucleotides, or that extend further along the FGFR1 pre-mRNA or mRNA in either the 3' or 5' direction than the preferred embodiments, or which comprise a sequence which is substantially complementary to and specifically binds to at least a portion of the targeted FGFR1 alpha exon but which also inhibit cell proliferation are also within the scope of the invention.

The term "oligomer" or "oligonucleosidel" refers to a chain of nucleosides which are linked by internucleoside linkages which is generally from about 4 to about 100 nucleosides in length, but which may be greater than about 100 nucleosides in length. They are usually synthesized from nucleoside monomers, but may also be obtained by enzymatic means. Thus, the term "oligomer" refers to a chain of oligonucleosides which have internucleosidyl linkages, linking nucleoside monomers and, thus, include deoxy- and ribo-oligonucleotides, nonionic oligonucleoside alkyl- and aryl-phosphonate analogs, alkyl- and aryl-phosphonothioates, phosphorothioate or phosphorodithioate analogs of oligonucleotides, phosphoramidate analogs of oligonucleotides, neutral phosphate ester oligonucleoside analogs, such as phosphotriesters and other oligonucleoside analogs and modified oligonucleosides, and also nucleoside/non-nucleoside polymers. The term also includes nucleoside/non-nucleoside polymers wherein one or more of the phosphorus group linkages between monomeric units has been replaced by a non-phosphorous linkage such as a formacetal linkage, a thioformacetal linkage, a morpholino linkage, a sulfamate linkage, a silyl linkage, a carbamate linkage, an amide linkage, a guanidine linkage, a nitroxide linkage, or a substituted hydrazine linkage. These analogs may be additionally modified to contain 2'O-alkyl substitutions to alter binding affinity with DNA and RNA targets. It also includes nucleoside/non-nucleoside polymers wherein both the sugar and the phosphorous moiety have been replaced or modified such as morpholino base analogs, or polyamide base analogs. It also includes nucleoside/non-nucleoside polymers wherein the base, the sugar, and the phosphate backbone of the non-nucleoside are either replaced by non-nucleoside moiety or wherein a non-nucleoside moiety is inserted into the nucleoside/non-nucleoside polymer, optionally, said non-nucleoside moiety may serve to link other small molecules which may interact with target sequences or alter uptake into target cells.

It is preferable to use chemically modified derivatives (i.e. derivatized oligomers) or analogs of antisense oligomers in the performance of the invention rather than "native" or unmodified oligodeoxynucleotides. "Native" oligodeoxynucleotides can be conveniently synthesized with a DNA synthesizer using standard phosphoramidite chemistry. Suitable derivatives, and methods for preparing the derivatives, involve alterations that (1) increase the oligomer's resistance to nuclease, for example, methylphosphonate (35), alpha-deoxynucleotides (36), and 2'-O-methyl-ribonucleosides (37); (2) increase the affinity of the oligomer to the target, for example, covalently-linked derivatives such as acridine (38); and (3) increase the cleavage ratio, for example, Fe-ethylenediamine tetraacetic acid (EDTA) and analogues (43), 5-glycylamido-1, 10-o-phenanthroline (44), and diethylenetriaamine-pentaacetic acid (DTPA) derivatives (45). Other suitable derivatives include, but are not restricted to, phosphorothioate and dithioate (34), alkylated oligomers (e.g., N-2-chlorocethylamine) (39,40), phenazine (41), 5-methyl-$N^4$-$N^4$-ethanocytosine (42), and various chimeric oligonucleosides comprised of the above-stated modifications and derivatives. All of the above publications are hereby specifically incorporated by reference as if fully set forth herein.

Analogs of the present invention include combinations of the above-mentioned modifications involving linkage groups and/or structural modifications of the sugar or base for the purpose of improving RNAseH-mediated destruction of the targeted RNA, binding affinity, nuclease resistance, and or target specificity.

Thus, it will be seen that the present invention provides synthetic oligomers having one or more segments including mixed internucleosidyl linkages, particularly oligomers having chirally pure or enriched phosphonate internucleosidyl linkages interspersed with single non-phosphonate internucleosidyl linkages and methods for their preparation. Such phosphonate internucleosidyl linkages include lower alkylphosphonate internucleosidyl linkages of 1 to 3 carbon atoms and lower alkylphosphonothioate (alkylthiophosphonate) internucleosidyl linkages of 1 to 3 carbon atoms. These mixed oligomer segments preferably have phosphonate internucleosidyl linkages interspersed between single non-phosphonate internucleosidyl linkages in a ratio of from 1 to about 1 to 1 to about 4 non-phosphonate linkages to phosphonate linkages. According to a preferred aspect, such oligomers have alternating chirally pure phosphonate internucleosidyl linkages which alternate with non-phosphonate internucleosidyl linkages. Oligomers comprising such segments, particularly in one or more non-RHaseH-activating regions, may be used to prevent or interfere with expression or translation of a single-stranded RNA target sequence. The chimeric oligonucleosides have an overall nucleoside base sequence, including the RHaseH-activating and non-RHaseH-activating regions, which is sufficiently complementary to the RNA target sequence to hybridize therewith.

Preferred chirally pure phosphonate linkages include $R_p$ lower alkylphosphonate linkages, and more preferred are $R_p$ methylphosphonate internucleosidyl linkages. Preferred non-phosphonate linkages include phosphodiester, phosphorothioate and phosphorodithioate. According to an especially preferred aspect, $R_p$-enriched oligomers are provided having chirally pure $R_p$-methyl phosphonate linkages which alternate with phosphodiester linkages in the non-RHaseH-activating region of the compound. These alternating oligomers have been found to exhibit enhanced binding affinity for an RNA target sequence and also increased nuclease resistance and specificity.

The present invention likewise includes chimeric antisense oligomers having enhanced potency as antisense inhibitors of gene expression comprising one or more segments with methylphosphonate internucleosidyl linkages enhanced for the $R_p$ configuration which are interspersed between non-phosphonate internucleosidyl linkages, preferably phosphodiester or alternatively phosphorothioate or phosphorodithioate linkages.

Chimeric oligomers of the invention, or segments thereof, having a predetermined base sequence of nucleosidyl units and having chirally pure phosphonate internucleosidyl linkages mixed with non-phosphonate linkages wherein the phosphonate linkages are interspersed between single non-phosphonate linkages may be prepared by coupling to one another individual nucleoside dimers, trimers or tetrameres of preselected nucleoside base sequence having chirally pure or racemic phosphonate or other internucleosidyl linkages.

The chirally-selected methylphosphonate and other monomers, dimers, trimers and the like can be coupled together by a variety of different methods leading to the following, non-exclusive, types of internucleosidyl linkages: phosphodiester, phosphotriester phosphorothioate, phosphorodithioate, phosphoramidate, phosphorofluoridates, boranophosphates, formacetal, and silyl.

Utility and Administration

Derivatized oligomers may be used to bind with and then irreversibly modify a target site in a nucleic acid by cross-linking (psoralens) or cleaving (EDTA). By careful selection of a target site for cleavage, one of the strands may be used as a molecular scissors to specifically cleave a selected nucleic acid sequence.

The oligomers provided herein may be derivatized to incorporate a nucleic acid reacting or modifying group which can be caused to react with a nucleic acid segment or a target sequence thereof to irreversibly modify, degrade or destroy the nucleic acid and thus irreversibly inhibit its functions.

These oligomers may be used to inactivate or inhibit or alter expression of a particular gene or target sequence of the same in a living cell, allowing selective inactivation or inhibition or alteration of expression. The target sequence may be RNA, such as a pre-mRNA or an mRNA. mRNA target sequences include an initiation codon region, a coding region, a polyadenylation region, an mRNA cap site or a splice junction.

Since the oligomers provided herein may form duplexes or triple helix complexes or other forms of stable association with transcribed regions of nucleic acids, these complexes are useful in antisense therapy.

Many diseases and other conditions are characterized by the presence of undesired DNA or RNA, which may be in certain instances single stranded and in other instances double stranded. These diseases and conditions can be treated using the principles of antisense therapy as is generally understood in the art. Antisense therapy includes targeting a specific DNA or RNA target sequence through complementarity or through any other specific binding means, in the case of the present invention by formation of duplexes or triple helix complexes.

According to one aspect of the present invention, these antisense oligomers have a sequence which is complementary to a portion of the RNA transcribed from the selected target gene. Although the exact molecular mechanism of inhibition has not been conclusively determined, the duplexes so formed may inhibit translation, processing or transport of an mRNA sequence.

According to an alternate aspect of the present invention, interference with or prevention of expression, or translation of a selected RNA target sequence may be accomplished by triple helix formation using oligomers of the present invention as a triplex oligomer pair having sequences selected such that the oligomers are complementary to and form a triple helix complex with the RNA target sequence and thereby interfere with or prevent expression of the targeted nucleic acid sequence. Such triple strand formation can occur in one of several ways. Basically, two separate or connected oligomers may form a triple strand with the single stranded RNA. Accordingly, the antisense oligomers (including triplex oligomer pairs) of the present invention find use in preventing or interfering with the expression of a target sequence of double or single stranded nucleic acid functionally equivalent to the human FGFR1 gene by formation of triple helix complexes to achieve down regulation of the target FGFR1 gene thereby suppressing the growth of tumor cells.

As a general matter, the oligomers employed will have a sequence that is complementary to the sequence of the target nucleic acid. However, absolute complementarity may not be required; in general, any oligomer having sufficient complementarity to form a stable duplex (or triple helix complex as the case may be) with the target nucleic acid is considered to be suitable. Since stable duplex formation depends on the sequence and length of the hybridizing oligomer and the degree of complementarity between the antisense oligomer and the target sequence, the system can tolerate less fidelity (complementarity) when longer oligomers are used. This is also true with oligomers which form triple helix complexes. However, oligomers of about 8 to about 40 nucleosidyl units in length which have sufficient complementarity to form a duplex or triple helix structure having a melting temperature of greater than about 40° C. under physiological conditions are particularly suitable for use according to the methods of the present invention.

The oligomers for use in the instant invention may be administered singly, or combinations of oligomers may be administered for adjacent or distant targets or for combined effects of antisense mechanisms with the foregoing general mechanisms.

In therapeutic applications, the oligomers can be formulated for a variety of modes of administration, including oral, topical or localized administration. It may be beneficial to have pharmaceutical formulations containing acid resistant oligomers that may come in contact with acid conditions during their manufacture or when such formulations may themselves be made acidic, to some extent, in order to be more compatible with the conditions prevailing at the site of application. Techniques and formulations generally may be found in *Remington's Pharmaceutical Sciences*, Mack Publishing Co., Easton, Pa., latest edition. The oligomer active ingredient is generally combined with a carrier such as a diluent of excipient which may include fillers, extenders, binding, wetting agents, disintegrants, surface-active agents, erodible polymers or lubricants, depending on the nature of the mode of administration and dosage forms. Typical dosage forms include tablets, powders, liquid preparations including suspensions, emulsions and solutions, granules, and capsules.

Certain of the oligomers of the present invention may be particularly suited for oral administration which may require exposure of the drug to acidic conditions in the stomach for up to about 4 hours under conventional drug delivery conditions and for up to about 12 hours when delivered in a sustained release form. For treatment of certain conditions it may be advantageous to formulate these oligomers in a sustained release form. U.S. Pat. No. 4,839,177 to Colombo et al., the disclosure of which is incorporated herein by reference, describes certain preferred controlled-rate release systems. For oral administration, these oligomers may preferably have 2'-O-alkyl, more preferably 2'-O methyl, nucleosidyl units; these oligomers are formulated into conventional as well as delayed release oral administration forms such as capsules, tablets, and liquids.

Systemic administration of the claimed oligomers can be achieved by transmucosal or transdermal means, or the compounds can be administered orally. For transmucosal or transdermal administration, penetrants appropriate to the barrier to be permeated are used in the formulation. Such penetrants are generally known in the art, and include, for example, bile salts and fusidic acid derivatives for transmucosal administration. In addition, detergents may be used to facilitate permeation. Transmucosal administration may be through use of nasal sprays, for example, as well as formulations suitable for administration by inhalation, or suppositories.

The antisense oligomer of the present invention can also be combined with a pharmaceutically acceptable carrier for administration to a subject. Examples of suitable pharmaceutical carriers are a variety of cationic lipids, including, but not limited to N-(1-2,3-dioleyloxy)propyl)-n,n,n-trimethylammonium chloride (DOTMA) and dioleoylphophotidylethanolamine (DOPE)]. Liposomes are also suitable carriers for the antisense oligomers of the invention. Another suitable carrier is a slow-release gel or polymer comprising the claimed antisense molecules (92,93).

The antisense oligomers may be administered to patients by any effective route, including intravenous, intramuscular, intrathecal, intranasal, intraperitoneal, intratumoral, subcutaneous injection, in situ injection and oral administration. Oral administration may require enteric coatings to protect the claimed antisense molecules and analogs thereof from degradation along the gastrointestinal tract. The antisense oligomers may be mixed with an amount of a physiologically acceptable carrier or diluent, such as a saline solution or other suitable liquid. The antisense oligomers may also be combined with other carrier means to protect the antisense molecules or analogs thereof from degradation until they reach their targets and/or facilitate movement of the antisense molecules or analogs thereof across tissue barriers.

The present invention includes a method for suppressing the growth of tumor cells, including glioblastoma cells. The method involves the step of introducing the claimed antisense oligomer to the tumor cells which express the FGFR1 gene under conditions sufficient to reduce FGFR1 gene expression in the tumor cells. In an alternative embodiment of the claimed method, the step of introducing involves local delivery to brain tissue, which involves the step of surgically resecting the tumor, i.e. surgically removing as much of the tumor mass as feasible. A subsequent step involves localized introduction of the claimed antisense molecules to the cells of the tumor mass remaining at the site of resection. Localized introduction of the claimed antisense molecules to the tumor cells may involve placing slow release polymers comprising the claimed antisense molecules at the site of resection. The slow release polymers comprise a sufficient amount of the antisense molecules to inhibit the growth of the tumor cells. Methods for local delivery of compounds and compositions thereof to the brain are well known in the art (48,49). Other methods of local delivery involve stereotactic administration of intratumoral chemotherapy (50,51).

The antisense oligomers are administered in amounts effective to inhibit cancer or neoplastic cell growth, and in particular, glioblastoma cell growth in situ. The actual amount of any particular antisense oligomer administered will depend on factors such as the type and stage of cancer, the toxicity of the antisense oligomer to other cells of the body, its rate of uptake by cancer cells, and the weight and age of the individual to whom the antisense oligomer is administered. An effective dosage for the patient can be ascertained by conventional methods such as incrementally increasing the dosage of the antisense oligomer from an amount ineffective to inhibit cell proliferation to an effective amount. It is expected that concentrations presented to cancer cells, and in particular, glioblastoma cells, in the range of about 10 nM to about 30 μM will be effective to inhibit cell proliferation. Methods for determining pharmaceutical/pharmacokinetic parameters in chemotherapeutic applications of antisense oligonucleotides for treatment of cancer or other indications are known in the art (52).

The antisense oligomers are administered to the patient for at least a time sufficient to inhibit proliferation of the cancer cells. The antisense oligomers are preferably administered to patients at a frequency sufficient to maintain the level of antisense oligomers at an effective level in or around the cancer cells. To maintain an effective level, it may be necessary to administer the antisense oligomers several times a day, daily or at less frequent intervals. Antisense oligomers are administered until cancer cells can no longer be detected, or have been reduced in number such that further treatment provides no significant reduction in number, or the cells have been reduced to a number manageable by surgery or other treatments. The length of time that the antisense oligomers are administered will depend on factors such as the rate of uptake of the particular oligomer by cancer cells and time needed for the cells to respond to the oligomer.

The antisense oligomers of the invention may be administered according to the claimed method to patients as a combination of two or more different antisense oligomer/oligodeoxynucleotide sequences or as a single type of sequence. Accordingly, the claimed antisense oligomer, compositions thereof and methods of use include compositions of one or more claimed antisense oligomers, each having the claimed property of reducing the expression of at least one FGFR1 gene product and thereby suppressing the growth of tumor cells, the antisense oligomers mixed together and added simultaneously by the local delivery system.

The present invention further comprises vectors for transfecting human tumor cells. The claimed vector comprises a nucleotide sequence that encodes an antisense RNA which reduces the expression from the human FGFR1 gene. The antisense RNA expressed from the vector-delivered nucleotide sequence binds with a sequence portion of RNA expressed from the FGFR1 gene. The antisense RNA reduces the expression of at least one FGFR1 gene product, thereby suppressing the growth of the tumor cells. A preferred form of the antisense RNA is substantially complementary to and binds specifically to the FGFR1 alpha exon.

The present invention further involves a method using the claimed vector for suppressing the growth of tumor cells by introducing to tumor cells which express the FGFR1 gene the claimed antisense oligonucleotide as an RNA. The method comprises the step of transfecting the tumor with the claimed vector which comprises a sequence that encodes an antisense RNA which is substantially complementary to and binds the FGFR1 gene. A further step involves the expression of the sequence encoding the antisense RNA, which thereby results in reduction of FGFR1 gene expression in the tumor cells, and suppression of their growth.

Vectors for transfecting/transforming mammalian cells, which vectors comprise nucleotide sequences coding for antisense RNA that inhibit the expression of target genes are well known in the art (57). Techniques for constructing such vectors and methods of using such vectors for transforming mammalian cancer cells to suppress tumorigenicity through down regulation of oncogenes, protooncogenes, and other endogenous genes (e.g. FGFR1) have been widely reported (57). Protocols are also known for introducing an antisense RNA to tumor cells by transfecting tumor cells with a vector comprising a sequence that encodes an antisense RNA which is specific for and binds RNA expressed from a chosen target gene or RNA expressed from a chosen target locus comprising a specific sequence portion (57).

The growth inhibitory actions and the specificity of the claimed FGFR1-alpha exon-specific antisense oligomers demonstrated in the Examples below.

Examples

General Methods

The Examples below use the following protocols:

A. Cells and Cell Cultures.

The human cells used in these examples were SNB-19 and T98 cell lines, which were derived from high grade glioblastomas after culturing small fragments of tumor biopsies. Cell line T98 has been deposited in the American Type Culture Collection, and designated as ATCC CRL 1690. SNB-19 cells are described in Gross et al. (53). The derivation of these tumors was confirmed by histological analysis, as described in Gross et al. (53). The glioma cell lines, which were mycoplasma free, were maintained as described in Gross et al. (53).

B. Cell Growth and Dose Response.

Glioma cells were plated at $1 \times 10^5$ cells/8.0 cm$^2$ tissue culture well in serum supplemented medium (10%). Within 18–20 hours postplating, the serum-supplemented medium was removed and the cells were washed three times with phosphate-buffered saline (PBS) and converted to serum free medium (SFM). Antisense oligomers, including the claimed antisense oligomers, or the appropriate control oligonucleotides were solubilized in sterile water and added at a final concentration of 30 micromolar directly to the cells at the time of conversion to SFM. This was considered as day 1. The cells were treated for three consecutive days with antisense oligonucleotides. In the time course study (FIG. 3, Examples 2 and 3), one set of cells was additionally treated on days 7 and 8 with antisense or control oligonucleotides. One to eleven days later the cells were washed twice with PBS and removed from the tissue culture wells by trypsinization (0.25%) in PBS. Cell number was determined using a hemocytometer. After being counted, cells were pelleted and used for mRNA purification and PCR analysis.

C. RNA-PCR Analysis.

Relative levels of expression of FGFR1α and FGFR1β transcripts in cell lines were determined by RNA-PCR analysis. Poly A [plus] mRNA was extracted using the MicroFast Tract kit as per instructions of the manufacturer (Invitrogen, San Diego, Calif.). For tumor and adjacent brain, RNA was extracted from 20 frozen sections (4 microns). First-strand DNA synthesis was performed using a cDNA cycle kit (Invitrogen) and random primers. For analysis of human FGFR1, nucleotide primers P1a (SEQ ID NO. 2), corresponding to nucleotides −67 to −44 at the 5' end, and P1b (SEQ ID NO. 3), complementary to nucleotides 1014–1035 at the 3' end of the mRNA for FGFR1 (55).

For analysis of human FGFR2, nucleotide primers P1a-R2 (SEQ ID NO. 4) (5'-AAGTGTGCAGATGGG ATTAACGTC-3'), corresponding to nucleotides 113–136 at the 5' end and P1b-R2 (SEQ ID NO. 5) (5'-ATTACC CGCCAAGCACGTATAT-3') complementary to 1196–1217 at the 3' end of the mRNA for FGFR2 were used.

PCR was generally performed for 3 cycles at 96° for 30 seconds, 64° for 15 seconds, and 72° for 60 seconds with a Perkin Elmer Cetus Gene Amp PCR system 9600. As a control for mRNA loading, GAPDH (glyceraldehyde 3-phosphate dehydrogenase) cDNA was amplified using nucleotide primers corresponding to nucleotides 27–46 at the 5' end (5'ACGGATTTGGTCGTATTGGG-3') (SEQ ID NO. 6) and complementary to nucleotides 238–257 (5'-TGATTTTGGAGGGATCTCGC-3') (SEQ ID NO. 7) at the 3' end of mRNA for GAPDH (56). Conditions were the same as those used for FGFR1. The GAPDH amplification product was radiolableled with $^{32}$P-dCTP during the final two PCR cycles (32 total cycles), run on a 6% polyacrylamide gel and exposed to x-ray film. Reaction mixtures (25 microliters) contained 10 mM Tris-HCl (pH 8.3), 1.5 mM MgCl$_2$, 50 mM KCl, 0.1 mg/ml gelatin, 0.8 units of Taq polymerase (Perkin Elmer-Cetus), 0.20 mM dNTPs and 0.5 micromolar of each primer. Relative levels of FGFR1α and FGFR1β transcripts were determined by PCR-Southern blot analysis. PCR products were separated on 1.5% agarose gels and transferred to nylon membrane filters (Hybond-N, Amersham). The filters were hybridized to a $^{32}$P-labeled FGFR1 oligonucleotide complementary to nucleotides 610–630 (55) which is derived from a sequence common to alpha, beta, and gamma isoforms (5'ATAACGGAC CTTGTAGCCTCC-3') (SEQ ID NO. 8) and internal to PCR primers P1a and P1b. FGFR2 amplification was monitored using an oligonucleotide corresponding to nucleotides 192–212 (5'-GGTCGTTTCATCTGCCTGGTC-3') (SEQ ID NO. 9) (Dionne et al., 1990b). FGFR1 and FGFR2-specific oligonucleotides only hybridized with their respective amplification product. Signal intensity was measured directly from the hybridized nylon membrane using a PhosphorImager (Molecular Dynamics). PCR amplification was evaluated through a range of 20 to 40 cycles. Accumulation of PCR amplification products was linear through 35 cycles as previously described (32). FGFR1β/FGFR1α ratios were constant over the linear range of amplification. All PCR-Southern blots were performed a minimum of three times for every sample.

D. Preparation of Cell Extracts.

Cultured cells were homogenized in a buffer of 10 mM Tris-HClpH 7.0, 2M NaCl and 0.1% CHAPS (3-3-cholamidopropyl-dimethylammonio-1-propanesulfonate) detergent containing the protease inhibitors leupeptin, 10 micrograms/ml, 0.2 mM PMSF (phenylmethyl sulfonylfluoride), and 100 micrograms/ml of pepstatin, bestatin and aprotinin (Boehringer Mannheim). The homogenate was centrifuged at 14,000×g for 30 minutes. The supernatant was removed and stored at −800° C. Aliquots were taken for protein determinations using the Bio-Rad protein detection systems (Hercules, Calif.). Supernatants were either analyzed directly by sodium dodecyl sulfate-polyacrylamide gel electrophoresis (SDS-PAGE) or first incubated with Heparin-Affigel (Bio-Rad) to concentrate heparin-binding proteins.

Extracts to be enriched for heparin binding proteins were diluted 1:5 in PBS and incubated overnight with 50 microliters of Heparin-Affigel at 4° C. This volume of Heparin-Affigel binds at least 1 microgram of purified human recombinant bFGF (hr-bFGF, Synergen, Boulder, Colo.). Heparin-Affigel was then centrifuged at 14,000×g for 10 minutes and the supernatant was removed. The Heparin-Affigel was rinsed three times in PBS and proteins were eluted by boiling for 5 minutes in sample buffer containing 5% 2-mercaptoethanol and 2.5% SDS.

E. Gel Electrophoresis and Western Blot Analysis.

Heparin-binding proteins were resolved by SDS-PAGE using a 15% gel and transferred to nitrocellulose. Nonspecific sites were blocked by incubating nitrocellulose in TBST (10 mM Tris-HCl pH 8.0, 150 mM NaCl, 0.05% Tween 20) containing 5% powdered milk. Blots were either stained with Poncau red or incubated overnight with the anti-bFGF monoclonal antibody. DE6 at a 1:1000 dilution. In control experiments, blots were incubated in TBST in the absence of primary antibody or with protein A purified mouse IgG. Blots were washed three times for 10 minutes each in TBST and subsequently incubated with a biotin-conjugated goat anti-mouse secondary antibody (Amersham) (1:500) for 45 minutes at room temperature. The blots were washed three times for 10 minutes each in TBST and subsequently incubated with a streptavidin (1:1000)-biotinylated horseradish peroxidate (1:2500) complex in TBST for 45 minutes at room temperature. The blots were then washed four times for 10 minutes each in TBST. Immunoreactive bands were visualized by developing the blot with Amersham ECL reagents according to the manufacturer's specifications. Following a one-minute exposure to the ECL reagents, the blots were covered with Saran Wrap and exposed to x-ray film for 10–12 minutes. The molecular weights of bFGF proteins were determined by comparison with biotinylated markers (Bio-Rad) and a human recombinant bFGF standard (Synergen, Boulder, Colo.).

Example 1

Preparation of Antisense Oligomers

Synthesis of phosphorothioate oligonucleotides in a 3' to 5' direction was achieved on a solid support. A dimethoxytrityl (DMT) protected starting nucleoside attached to solid support such as controlled pore glass was placed in a reaction vessel (300 µmoles). The DMT protecting group is removed with deblock (2.5% v/v dichloroacetic acid in dichloromethane, 30 eq) with repeated treatment (4–7 times depending on the base) to insure complete removal of the protecting group. The support was washed with acetonitrile to remove excess acid from the support. The desired β-cyanoethyl phosphoramidite nucleoside (2 eq. with respect to starting nucleoside on support) was mixed with ethylthiotetrazole (6 eq) under argon stirring for 5 minutes. The excess monomer and activator were washed off the support with acetonitrile. The phosphite intermediate was sulfurized for 10 minutes with 3H-1,2-benzodithiole-3-one 1,1 dioxide (Beaucage reagent, 5 eq.). Cap A (40% acetic anhydride in THF) and Cap B (0.625% DMAP in pyridine were mixed and used to cap off excess alcohols that were not coupled to the amidite monomer. The whole cycle was then repeated until the desired length oligomer had been synthesized.

The final DMT was removed with deblock as described above. The support was then placed in a pressure vessel and the oligomer was removed from the support and the base labile protecting groups on the heterocyclic amines removed with concentrated ammonium hydroxide. The solid support was filtered away from the ammonium hydroxide solution and the ammonia removed in vacuo. The residue was taken up in the mobile phase for the purification and the oligonucleotides purified by ion-exchange chromatography to give material that was >97% pure. The usual yields were around 1.5 mg/µmole of starting material.

Example 2

Effect of Claimed Antisense Oligomer on Glioblastoma Cell Growth

Using the general methods described above, the inventor examined the effects of FGFR1α-exon specific antisense oligomers on growth of human glioblastoma cells.

The following phosphorothioate oligomers, synthesized as described above in Example 1, were introduced at concentrations of 30 µM to glioblastoma cells:

R2AS$_{ini}$ (SEQ ID NO. 12) is FGFR2-initiation site exon-specific antisense oligonucleotide.

R1AS$_β$ (SEQ ID No. 11) is FGFR1β exon specific antisense oligonucleotide.

R1AS$_α$ (SEQ ID NO. 1) is FGFR1α exon specific antisense oligonucleotide.

Figure 2:
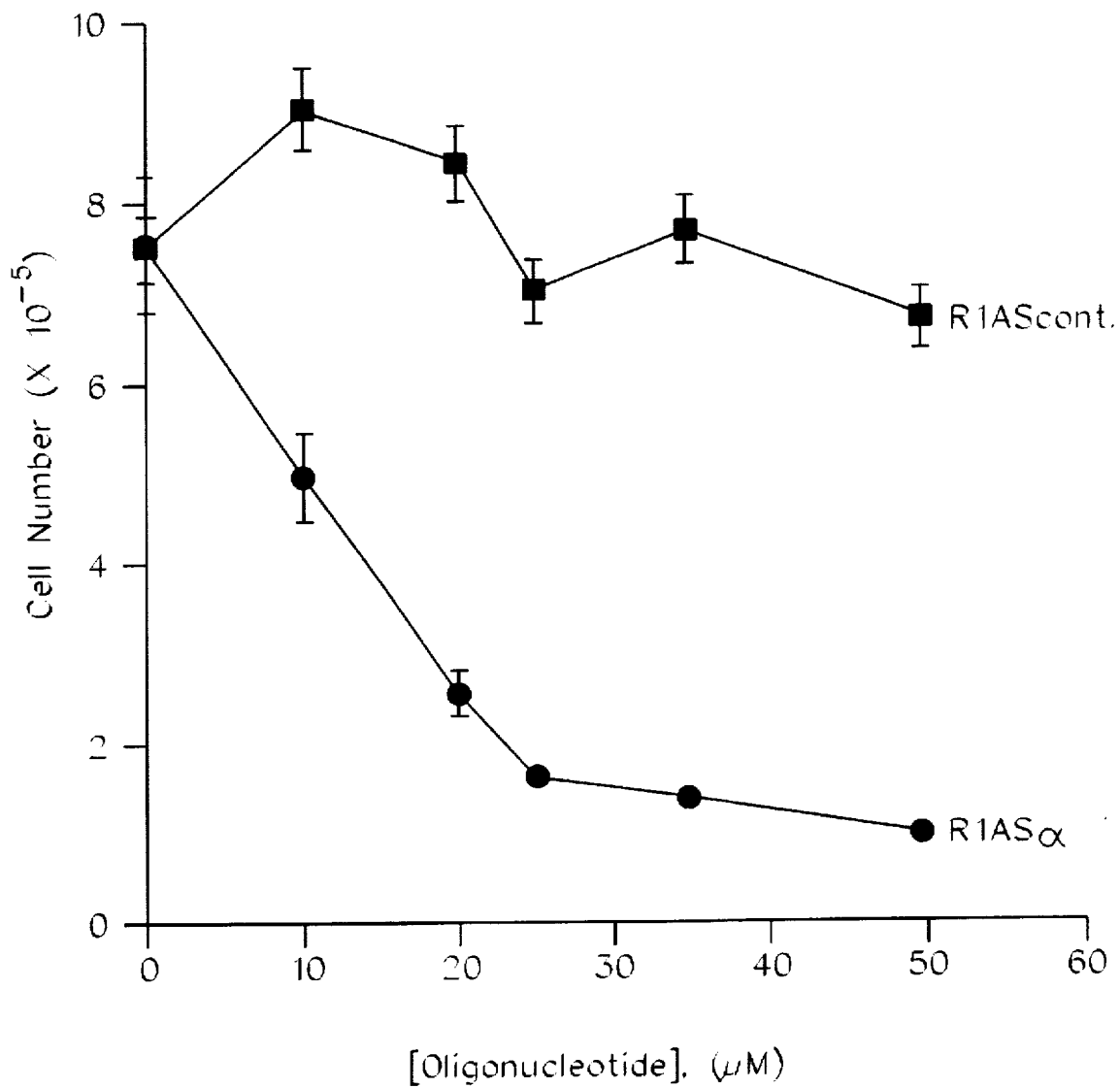
FIG. 2 shows a dose-response curve for the alpha antisense and reverse control oligomers.
Figure 3:
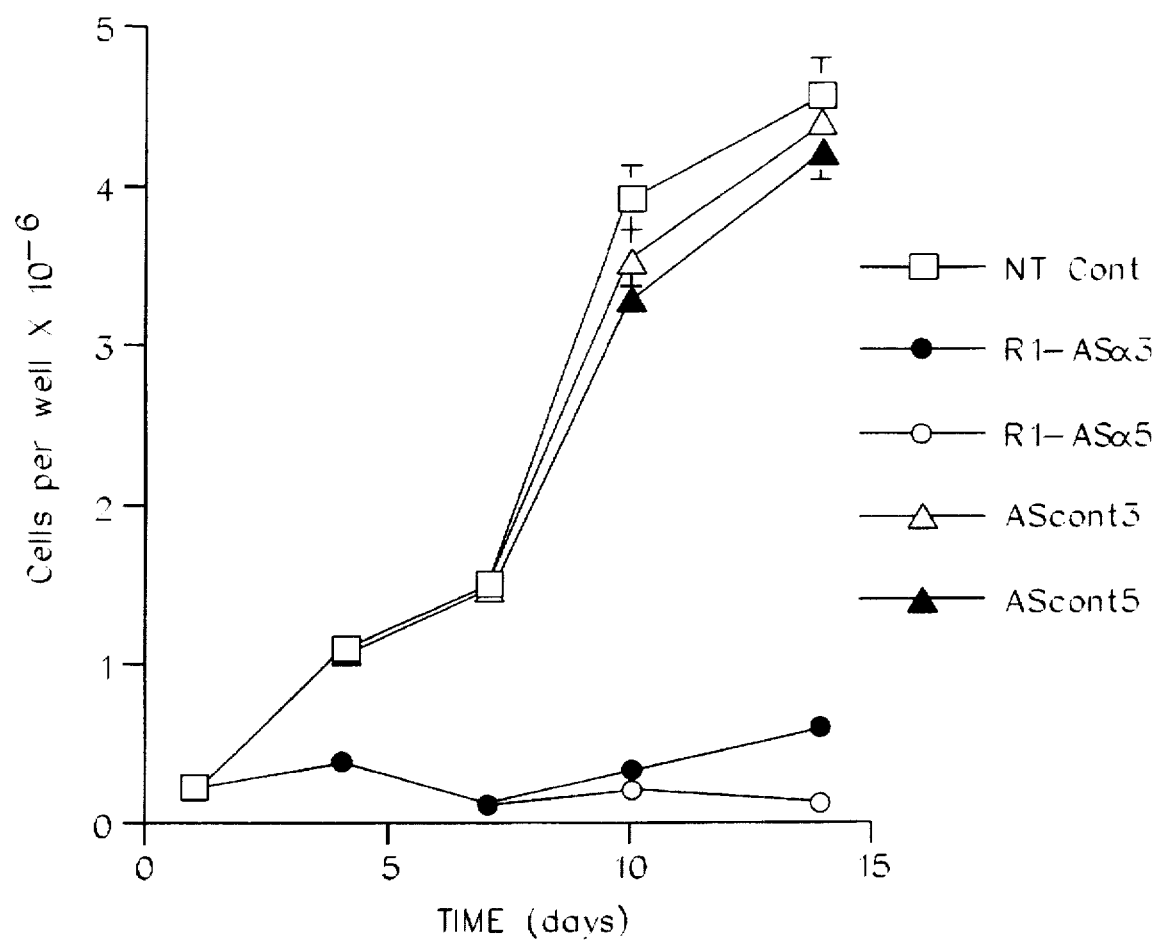
FIG. 3 shows a time course displaying the effects of multiple treatments using antisense and control oligomers on glioblastoma cell growth.

R1AS$_{ini}$ (SEQ ID NO. 13) is FGRR1-initiation site exon specific antisense oligonucleotide R1AS$_{cont}$ (SEQ ID NO. 10) is FGFR1α-exon specific antisense oligonucleotide in the reverse orientation As shown in FIGS. 1, 2 and 3, the introduction of FGFR1α-exon-specific antisense oligonucleotide (R1ASα) to human glioblastoma cells at a concentration of 30 µM resulted in a consistent and highly reproducible 70–80% reduction in cell density. The effect was saturable and dose-dependent. This finding indicates the effectiveness of antisense oligomer which specifically binds to at least a portion of pre-mRNA or RNA, or at least a portion of the alpha exon pre-mRNA or RNA, expressed from the human FGFR1 gene for suppressing the growth of tumor cells, and, in particular, glioblastoma cells. In FIG. 1, the bar designated "Cont" stands for control cells, which were not treated with oligomer.

Example 3

Effects of Control Oligomers on Glioblastoma Cell Growth

Using the general methods described above, the inventor examined the effects of control antisense oligomers on growth of human glioblastoma cells.

The addition of the following control oligonucleotides had no significant effect on glioblastoma cell density in culture when used at equal or greater concentrations than the effective antisense oligomer of the invention:

(a) FGFR1α-exon specific antisense oligonucleotide in the reverse orientation (R1AS$_{cont}$) (SEQUENCE ID NO. 10);

(b) FGFR2-initiation site exon-specific antisense oligonucleotide (R2ASini) (SEQUENCE ID NO. 12).

The effect of FGFR1β specific antisense oligonucleotide (R1ASβ) (SEQUENCE ID NO. 11) on glioblastoma cell density was also examined.

The FGFRα-exon specific antisense oligonucleotide (R1AS$_{cont}$) (SEQUENCE ID NO. 10) in the reverse orientation was an important control because it maintained an identical base composition to the effective antisense oligonucleotide and its lack of effectiveness in suppressing cell growth was the result of its inability to specifically hybridize to the target message.

Figure 5:
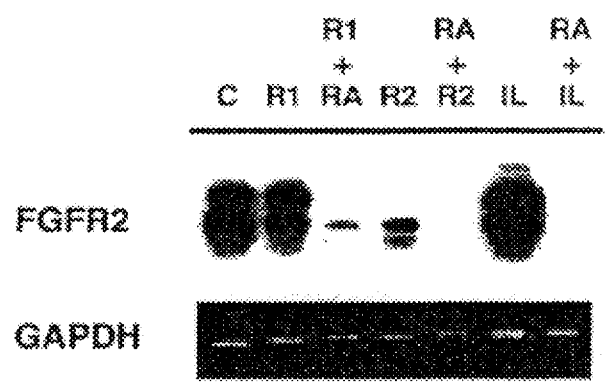
FIG. 5 is RT-PCR Southern Blot analysis of FGFR2 mRNA expression.
Figure 6:
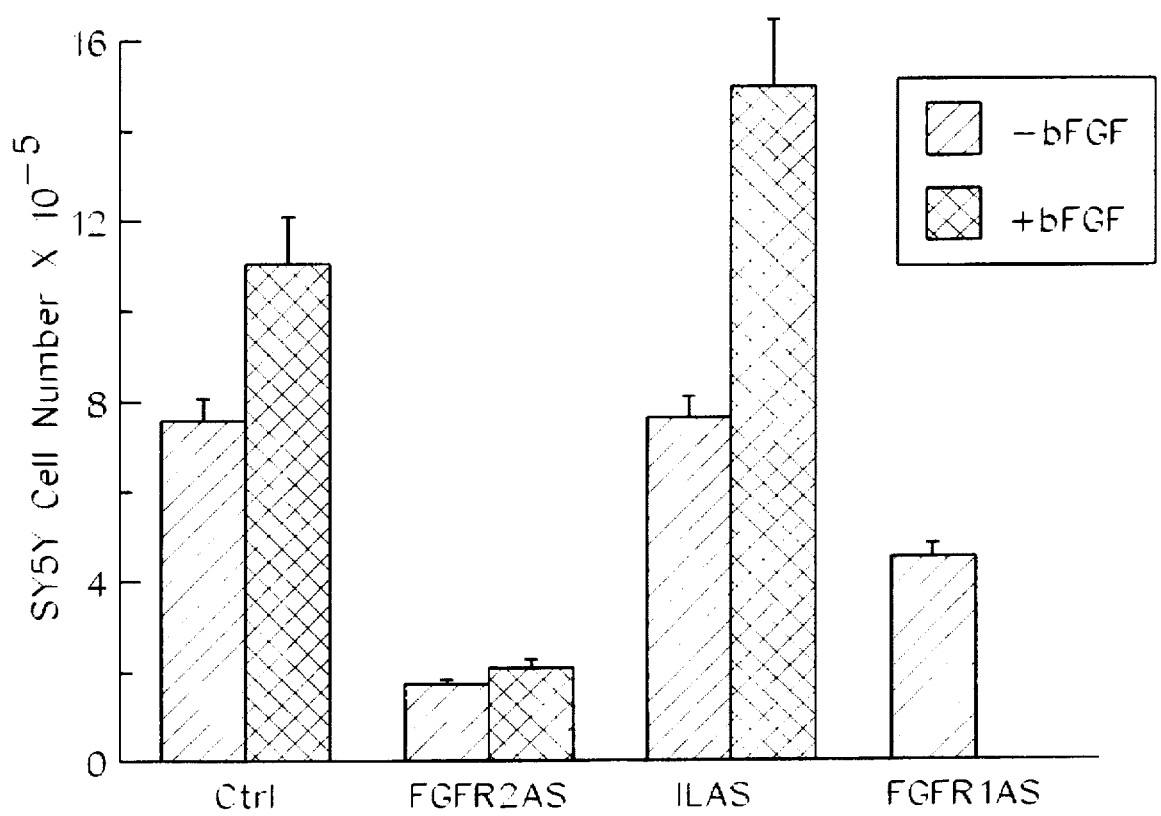
FIG. 6 shows the growth inhibitory actions of FGFR2 antisense initiation oligomers on SY5Y human neuroblastoma cell growth.

FIG. 1 shows that the addition of the FGFR2-initiation site exon-specific antisense oligonucleotide (R2ASini) (SEQ ID NO. 12) had no effect on glioblastoma cell growth but it significantly reduced the cellular density of the human neuroblastoma cell line SY5Y in culture (FIG. 6). It was further demonstrated (FIG. 5) that the SY5Y cell line expresses FGFR2 mRNA and that this mRNA was selectively reduced by the FGFR2-initiation site exon-specific antisense oligonucleotide. FIG. 6 demonstrates that the FGFR2 antisense oligonucleotide was effective in inhibiting cell growth in SY5Y but not effective in inhibiting growth of the human glioblastoma cell lines which were devoid of FGFR2 mRNA (FIG. 1). These results demonstrated that the FGFR2-initiation site antisense oligonucleotide is effective on cells expressing FGFR2. Therefore, the absence of an effect on glioblastoma cells in culture suggests that addition of any antisense oligonucleotide, even one to a related FGFR family member, was not sufficient to suppress cell growth.

The addition of FGFR1β antisense oligonucleotide to glioblastoma cells had no effect on cellular density (FIG. 1). This finding was not consistent in view of the observation that as astrocytic cells transform and progress from a normal cell to a malignant glioblastoma cell, the cells shift their expression of FGFR1 from an α predominant isoform (three immunoglobulin domains) to the β predominant isoform (two immunoglobulin domains). The β form represents as much as 70% to 90% of the FGFR1 message (32,33). The lack of an effect on cellular growth using the FGFR1β antisense oligonucleotide was as inconsistent a finding as finding an effect with the FGFR1α antisense oligonucleotide, since this α isoform represents a small fraction of the total message pool in human glioblastomas.

Example 4

Effect of Claimed Oligomers on FGFR1 mRNA Synthesis

Figure 4:
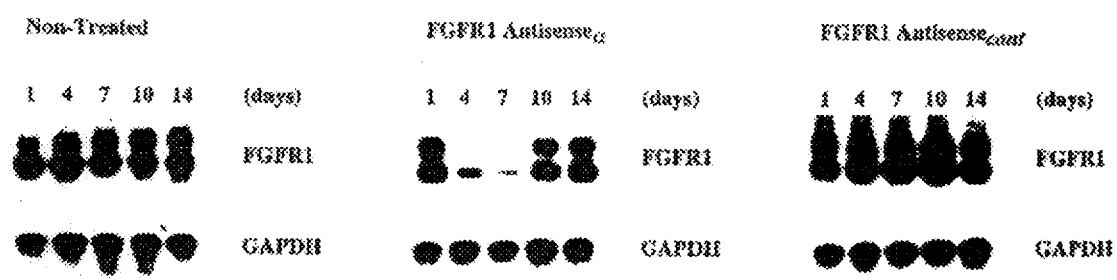
FIG. 4 is RT-PCR Southern Blot analysis of FGFR1 expression in antisense and control oligomer-treated glioblastoma cells.

The purpose of this Example was to determine the effects on FGFR1 mRNA synthesis of introducing the claimed antisense oligomer to glioblastoma cells. Using the general methods described above, it was demonstrated that the addition of the FGFR1α-exon-specific antisense oligonucleotide (SEQ ID NO. 1) selectively reduced the expression of FGFR1 mRNA (FIG. 4). In contrast, the FGFR1α-exon-specific antisense oligonucleotide in the reverse orientation (SEQ ID NO. 10) had no effect on FGFR1 mRNA levels, consistent with its inability to suppress growth (FIG. 4).

In experiments in which antisense oligonucleotide was added to the cells for three consecutive days and in which cell density was monitored for the subsequent two weeks, it was demonstrated that when the claimed FGFR1α-exon-specific antisense oligonucleotide (SEQ ID NO. 1) was not replenished, growth of the glioblastoma cells was reinitiated (FIG. 3) and this correlated with re-expression of FGFR1 mRNA (FIG. 4, days 10 and 14). Therefore, there was a clear correlation between the growth of the glioblastoma cells and their expression of FGFR1 mRNA.

Example 5

Effect of Claimed Oligomers on FGFR2 mRNA Synthesis

The purpose of this Example was to examine the effects on FGFR2 synthesis of introducing the claimed antisense oligomer to glioblastoma cells.

Using the methods described above, it was demonstrated that addition of the claimed FGFR1α-exon-specific antisense oligonucleotide did not effect the expression of FGFR2 mRNA in the human neuroblastoma cell line SY5Y (FIG. 5), which demonstrated the specificity of the FGFR1α-exon-specific antisense oligonucleotide for FGFR1; and further demonstrated the sequence-dependent action of the claimed FGFR1α-exon-specific oligonucleotide.

Figure 7:
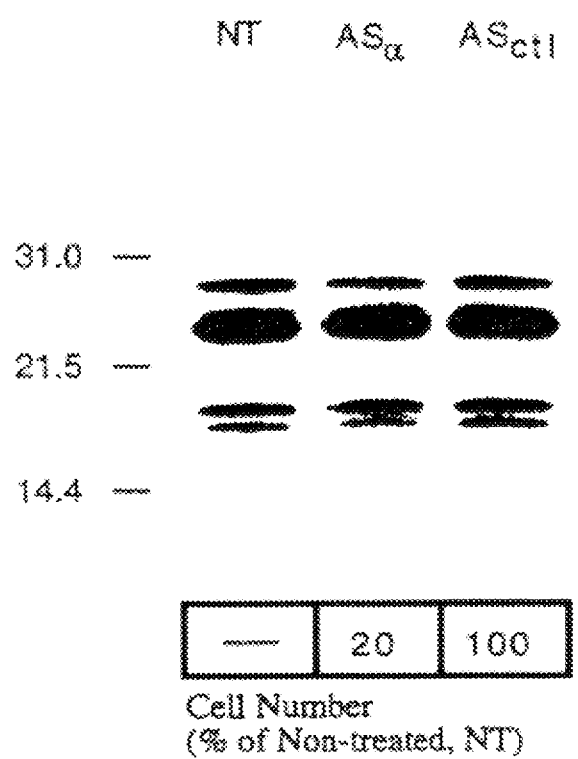
FIG. 7 is bFGF Western Blot analysis in FGFR1 alpha antisense and control treated glioblastoma cells.

It was further demonstrated that addition of FGFR1α-exon specific antisense oligonucleotide had no effect on the levels of basic fibroblast growth factor protein (FIG. 7). Basic fibroblast growth factor is a mitogen that has previously been shown to promote the growth of human glioblastoma cells.

The above results demonstrated a specific action, i.e. suppressing glioblastoma cell growth by the claimed antisense oligonucleotide through diminution of FGFR1 mRNA when, using the claimed method, the claimed antisense oligomer was brought into contact with tumor cells expressing the human FGFR1 gene.

Example 6

Effect of Claimed Antisense Oligomer on Growth of T98 Human Glioblastoma Cells

The purpose of this study was to determine the effect of the claimed antisense oligomer on the growth of another line of human glioblastoma cells, namely T98 cells. T98 cells were cultured and their numbers measured as described above.

Figure 8:
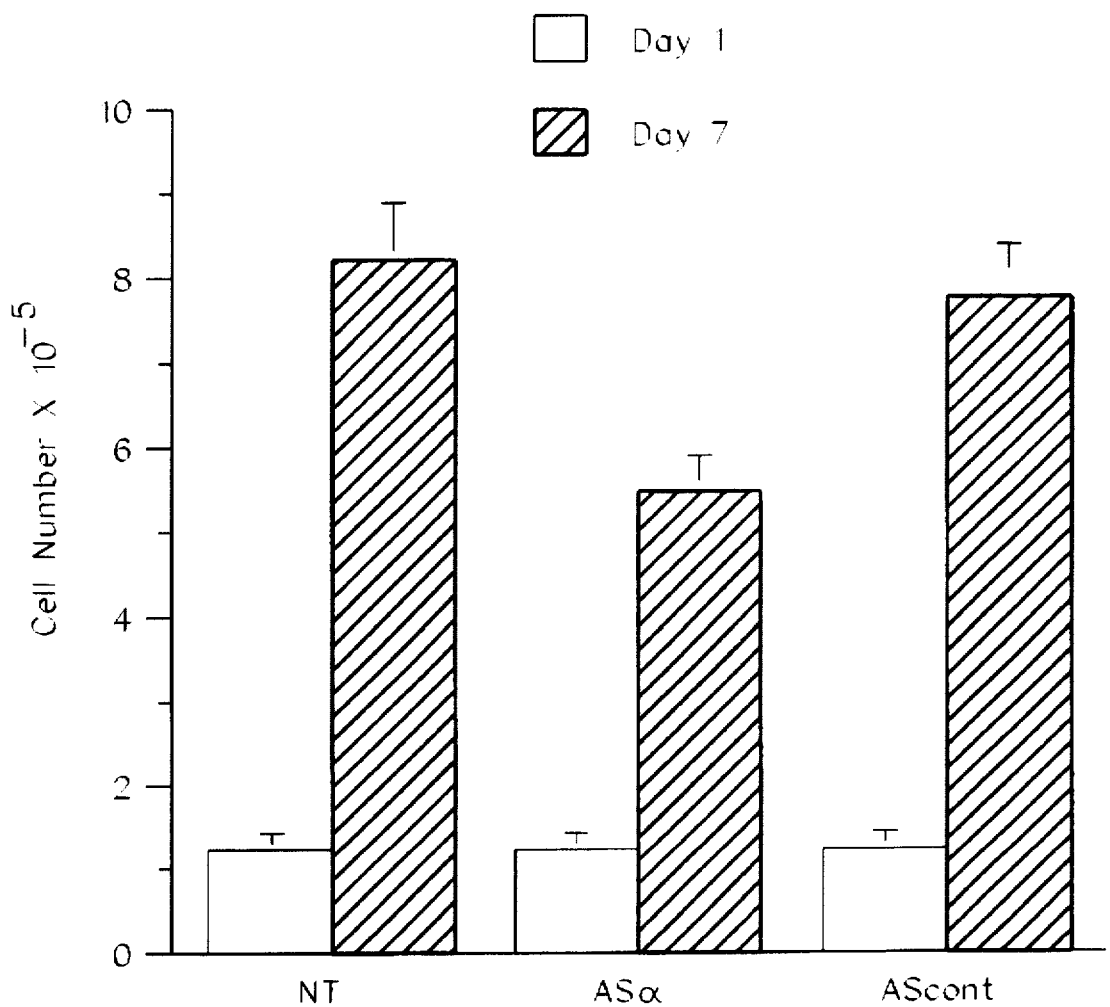
FIG. 8 shows the influence of FGFR1 antisense oligomers on the growth of T98 human glioblastoma cells in vitro.

30 μM FGFR1α-exon antisense oligonucleotide was added to the T98 cells. Cell densities were measured on days 1 and 7. As shown in FIG. 8, the addition of the claimed antisense oligomer resulted in a 34% reduction in cell number. No effect was observed with the control antisense oligonucleotide.

Example 7

Specificity of FGFR1 Alpha Exon Antisense Oligomer on Expression of FGFR Genes

The purpose of this work was to determine the selectivity of the FGFR1α-exon antisense oligomer on the expression of other FGFR genes in glioblastoma cells. This was done to rule out suspected cross-hybridization between the FGFR1α-exon antisense oligomer and other FGFR family member mRNAs, which could have led to the suppression of growth.

Cells were treated as described above.

mRNA was analyzed as described above with the exception that both FGFR1, FGFR3 and FGFR4 mRNA were studied in this particular work. SNB-19 glioblastoma cells were plated at $1 \times 10^5$ cells per 100 mm dish in serum-supplemented medium. Eighteen hours later the cells were converted to serum-free medium containing FGFR1α antisense oligonucleotide (R1ASα, 30 μm) or FGFR1α antisense reverse control oligonucleotide (R1αRC, 30 μm). Non-treated cells (NT) were run as a control. Cells were treated for three consecutive days with oligonucleotide. Cells were scraped on day 7 and mRNA and cDNA were purified and synthesized respectively. Using cDNA from each of the three different treatments, PCR was used to amplify cDNA for FGFR1, FGFR3, and FGFR4 receptors. SNB-19 cells do not produce FGFR2.

Figure 9:
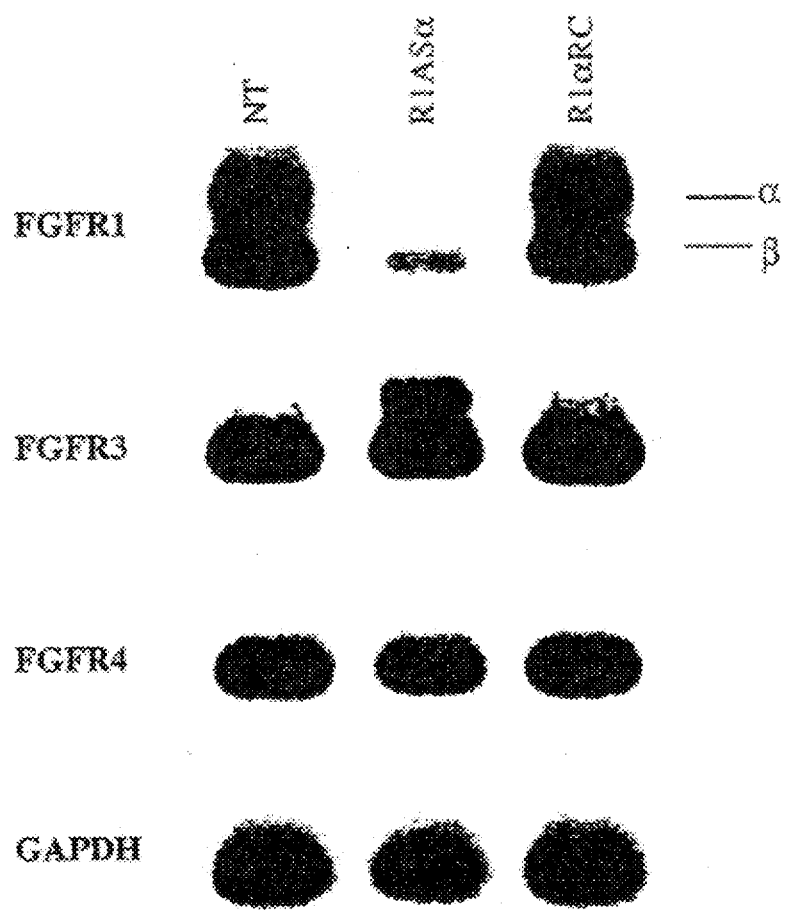
FIG. 9 shows an RT-PCR Southern Blot of FGFR1, FGFR3, and FGFR4 demonstrating the selective reduction of FGFR1 mRNA following treatment of glioblastoma cells with the antisense molecules of the invention.

As shown in FIG. 9, FGFR1 mRNA was suppressed while there was no effect on expression of the FGFR3 and FGFR4 gene, i.e the level of FGFR3 and FGFR4 mRNA was not diminished. FIG. 9 further shows no diminishment of the expression of the GAPDH (glyceraldehyde 3-phosphate dehydrogenase) locus. The findings demonstrated the specificity of the FGFR1α-exon antisense oligomer for the single and intended member of the FGFR family, namely FGFR1 mRNA. In particular, it was demonstrated that treatment with FGFR1α antisense oligonucleotide suppressed FGFR1 expression, whereas the reverse control oligonucleotide had no effect on FGFR1 expression. In addition, FGFR1α antisense oligonucleotide did not suppress the expression of FGFR3 or FGFR4, demonstrating the selective action of the claimed molecules' action on FGFR1. Although not limited to this explanation, it appeared that the significance of this finding was that the inhibition of growth was due only to the suppression of FGFR1, which is the intended target of this invention.

Example 8

Using the general methods referred to above, antisense oligomers having a greater or lesser number of substituent nucleotides, or that extend further along the FGFR1 pre-mRNA or mRNA in either the 3' or 5' direction than the oligomer of SEQUENCE ID NO. 1, or which comprise a sequence which is substantially complementary to and specifically binds to at least a portion of the targeted FGFR1 alpha exon are introduced to tumor cells expressing the FGFR1 gene. Introduction of the claimed antisense oligomers to tumor cells in suitable formulations described herein using therapeutic applications also described herein is found to suppress the growth of tumor cells in a variety of glioblastomas.

Having thus disclosed exemplary embodiments of the present invention, it should be noted by those skilled in the art that this disclosure is exemplary only and that various other alternatives, adaptations, and modifications may be made within the scope of the present invention. Accordingly, the present invention is not limited to the specific embodiments as illustrated herein, but is only limited by the following claims.

Bibliography (Listed in Sequential Order As Appears in Text)

(1) Takahashi, J. A., Mori, H., Fukumoto, M., Igarashi, K., Jaye, M., Oda, Y., Kikuchi, H., and Hatanaka, M. Gene Expression of Fibroblast Growth Factors in Human Gliomas and Meningiomas: Demonstration of Cellular Source of Basic Fibroblast Growth Factor mRNA and Peptide in Tumor Tissue. *Proc. Nat. Acad. Sci. USA* (1990) 87:5710–5714.

(2) Maxwell, M., Nabor, S. P., Wolfe, H. J., Hedley-Whyte, E. T., Galanopoulos, T., Neville-Goldon,, J., and Antoniades, H. N. Expression of Angiogenic Growth Factor Genes in Primary Human Astrocytomas May Contribute to Their Growth and Progression, *Cancer Research* 51:1345–1351 (1991).

(3) Yamanaka, Y., Friess, H., Buchler, M., et al. Overexpression of Acidic and Basic Fibroblast Growth Factors in Human Pancreatic Cancer Correlates With Advanced Tumor Stage, *Cancer Res.* 53:5289–5296 (1993).

(4) Houssaint, E., Blanquet, P. R. Champion-Arnaue, P., Gesnel, M. C. Torriglia, A., Courtois, Y., and Breathnach, R., Related fibroblast growth factor receptor genes exist in the human genome, *Proc. Natl. Acad. Sci. U.S.*, 87: 8180–8184 (1990).

(5) Johnson, D. E., Lu, J., Chen, H., Werner, S., and Williams, L. T., The human fibroblast growth factor receptor genes: common structural arrangement underlines the mechanisms for generating receptor forms that differ in their third immunoglobulin domain, *Mol. Cell Biol.*, 11: 4627–4634 (1991).

(6) Keegan, K., Johnson, D. E., Williams, L. T., and Hayman, M. J., Isolation of an additional member of the fibroblast growth factor receptor family, FGFR-3, *Proc. Natl. Acad. Sci. USA*, 88: 1095–1099 (1991).

(7) Partanen, J., Makela, T. P., Eerola, E., Korhonen, J., Hirvonen, H., Claesson-Welsh, L., and Alitalo, K., FGFR-4, A novel acidic fibroblast growth factor receptor with a distance expression pattern, *EMBO J.*, 10: 1347–1354 (1991).

(8) Ruta, M., Burgess, W., Bivol, D., Epstein J., Neiger, N., Kaplow, J. Crumley, G., Dionne, C., Jaye, M., and Schlessinger, J., Receptor for acidic fibroblast growth factor is related to the tyrosine kinase encoded by the fms-like gene (FLG), *Proc. Natl. Acad. Sci. USA*, 86: 8722–8726 (1989).

(9) Miki, T., Bottaro, D. P., Fleming, T. P., Smith, C. L., Burgess, W. H., Chan, A. M. L., ad Aaronson, S. A., Determination of legand-binding specificity by alternative splicing: two distinct growth factor receptors encoded by a single gene, *Proc. Natl. Acad. Sci. USA*, 89: 246–250 (1992).

(10) Morrison, R. S., Gross, J. L., Herblin, W. F., Reilly, T. M., LaSala, P. A., Alterman, R. L., Moskal, J. R., Kornblith, P. L., and Dexter, D. L., Basic fibroblast growth factor-like activity and receptors are expressed in a human glioma cell Line, *Cancer Res.*, 50: 2524–2529 (1990).

(11) Holt et al., *Mol. Cell Biol.* 8:963–973 (1988), and Wickstrom et al., *Proc. Natl. Acad. Sci.* U.S.A., 85:1028-1-32 (1988).

(12) Zamecnik and Stephenson, *Proc. Natl. Acad. Sci.* U.S.A., 75:280–284 (1978) and Zamecnik et al., *Proc. Natl. Acad. Sci.* U.S.A., 83:4143–4146 (1986).

(13) Morrison, R. S. Suppression of basic fibroblast growth factor expression by antisense oligodeoxynucleotides inhibits the growth of transformed human astrocytes. *J. Biol. Chem.*, 266: 728–734 (1991).

(14) Murphy, P. R., Sato, Y., and Knee, R. S., Phosphorothioate antisense oligonucleotides against basic fibroblast growth factor inhibit anchorage-dependent and anchorage-independent growth of a malignant glioblastoma cell line. *Mol. Endocrinol.*, 6: 877–884 (1992).

(15) Becker, D., Lee., P. L., Rodeck, U., and Herlyn, M. (1992)) Inhibition of the Fibroblast Growth Factor Receptor 1 (FGFR1) Gene in Human Melanocytes and Malignant Melanomas Leads to Inhibition of Proliferation and Signs Indicative of Differentiation, *Oncogene* 7:2303–2313).

(16) John Goodchild, Conjugates of Oligonucleotides and Modified oligonucleotides: A Review of Their Synthesis and Properties, *Bioconjugate Chemistry*, Volume 1 No. 3, May/June (1990).

(17) Kan M., DiSorbo D., Hou J., Hoshi H., Mansson P. E., and McKeehan W. L., High and low affinity binding of heparin-binding growth factor to a 130-kDa receptor correlates with stimulation and inhibition of growth of a differentiated human hepatoma, *Cell J Biol Chem* (1988) 263:11306–11313.

(18) Moscatelli D., High and low affinity binding sites for basic fibroblast growth factor on cultured cells: Absence of a role for low affinity binding in the stimulation of plasminogen activator production by bovine capillary endothelial cells. *J Cell Physiol* (1987) 131:123–130.

(19) Vlodavsky I., Folkman J., Sullivan R., et al., Endothelial cell-derived basic fibroblast growth factor: Synthesis and deposition into subendothelial extra cellular matrix, *Proc Natl Acad Sci USA* (1987) 84:2292–2296.

(20) Yayon A., Klagsbrun M., Esko J. D., Leder P., and Ornitz D. M., Cell surface, heparin-like molecules are required for binding of basic fibroblast growth factor to its high affinity receptor, *Cell* (1991) 64:841–848.

(21) Rapraeger A. C., Krufka A., and Olwin B. B., Requirement of heparin sulfate for BFGF-mediated fibroblast growth and myoblast differentiation, *Science* (1991) 252:1705–1708.

(22) Johnson, D. E. and William L. T., Structural and Functional Diversity in the FGF Receptor Multigene Family, *Advances in Cancer Research* 60:1–41 (1993).

(23) Halaban R., Ghosh S., and Baird A., bFGF is the putative natural growth factor for human melanocytes In Vitro Cell Dev. Biol. (1987) 23:47–52.

(24) Rubin J. S., Osada H., Finch P. W., Taylor W. G., Rudikoff S., and Aaronson S. A., Purification and characterization of a newly identified growth factor specific for epithelial cells, Proc Natl Acad Sci USA (1989) 86:802–806.

(25) Peters K. G., Werner S., Chen G., and Williams L. T., Two FGF receptor genes are differentially expressed in epithelial and mesenchymal tissues during limb formation and organogenesis in the mouse, Development (1992) 114:233–243.

(26) Werner S., Duan D.-S. R., de Vries C., Peters K. G., Johnson D. E., and Williams L. T., Differential splicing in the extracellular region of fibroblast growth factor receptor 1 generates receptor variants with different ligand-binding specificities, Mol Cell Biol (1992) 12:82–88.

(27) Eisemann A., Ahn J. A., Graziani G., Tronick S. R., and Ron D., Alternative splicing generates at least five different isoforms of the human basic-FGF receptor, Oncogene (1991) 6:1195–1202.

(28) Hou J., Kan M., Wang F, et al., Substitution of putative half-cystine residues in heparin-binding fibroblast growth factor receptors, J Biol Chem (1992) 267(25):17804–17808.

(29) Lai C., and Lemke G., An extended family of protein-tyrosine kinase genes differentially expressed in the vertebrate nervous system, Neuron (1991) 6:691–704

(30) Peters K. G., Werner S., Chen G., and Williams L. T., Two FGF receptor genes are differentially expressed in epithelial and mesenchymal tissues during limb formation and organogenesis in the mouse. Development (1992) 114:233–243).

(31) Adnane, J., Guadray, P., Dionne, C. A., Crumley, G., Jaye, M., Schlessinger, J., Jeanteur, P., Birnbaum, D., and Theillet, C. BEK and FLG, Two Receptors to Members of the FGF family, Are Amplified in Subsets of Human Breast Cancer, Oncogene 6:659–663 (1991).

(32) Yamaguchi et al. PNAS 91:484 (1994)

(33) Morrison et al. Cancer Research 54:2794 (1994).

(34) Stein et al., Nucl. Acids Res., 16:3209–3221 (1988).

(35) Blake et al., Biochemistry 24:6132–6138 (1985).

(36) Morvan et al., Nucl. Acids Res.. 14:5019–5032 (1986).

(37) Monia et al. Evaluation of 2'-modified oligonucleotides containing 2' deoxy gaps as antisense inhibitors of gene expression. J. Biol. Chem. 268:14514–14522 (1933).

(38) Asseline et al., Proc. Natl Acad. Sci. U.S.A. 81:3297–3201 (1984).

(39) Knorre et al., Biochemie 67:783–789 (1985)

(40) Vlassov et al., Nucl. Acids Res. 14:4065–4076 (1986).

(41) Knorre et al., supra, and Vlassov et al., supra.

(42) Webb et al., Nucl. Acids Res. 14:7661–7674 (1986).

(43) Boutorin et al., FEBS Letter's 172:43–46 (1984).

(44) Chi-Hong et al., Proc. Natl. Acad. Sci. U.S.A. 83:7147–7151 (1986).

(45) Chu et al., Proc. Natl. Acad. Sci. 82:963–967 (1985).

(46) Domb, A. J., Implantable Biodegradable Polymers for Site-specific Drug Delivery, p.1, Polymeric Site-Specific Pharmacotherapy, J. Wiley and Sons, 1994.

(47) Brem, H., Walter, A., Tamargo, A., Olivi, R. and Langer, R., Drug Delivery to the Brain, p. 117, Polymeric Site-Specific Pharmacotherapy, J. Wiley and sons, 1994.

(48) Tamargo, B. H., Olivi, A., Pinn, M., Weingart, J. D., Wharam, M., Epstein, J, I., Biodegradable Polymers for Controlled Delivery of Chemotherapy With and Without Radiation Therapy in the Monkey Brain, J. Neurosurg (U.S.) 80(2):238–290 (1994).

(49) Tamargo, R. J., Mysero, J. S., Epstein, J. I., Yang, M. B., Chasin, M., and Brem, H. Interstitial Chemotherapy of the 9L Gliosarcoma: Controlled Release Polymers for Drug Delivery In the Brain, Cancer Res. (U.S.) 53(2):329–333 (1993).

(50) Bouvier, G., Penn, Kroin, J. S., Beique, R. A., Guerard, M.-J., Lesage, J., Appl. Neurophysiol. 50:223–226 (1987).

(51) Berger, M. S., Spence, A. M., Stelzer, K. J., "Brain Tumors," in Current Therapy in Hematology/Oncology, eds. Brain, M. C. and Carbone, P. P., publ. Mosby Publishers, Inc., Phil.

(52) Pharmacokinetics and Cancer Therapy, eds. P. Workman and M. A. Graham, volume 17 in Cancer Surveys, Cold Spring Harbor Laboratory Press, 1993 and in Pharmacokinetics, Milo Gibaldi and Donald Perrier, eds., 2nd ed., Marcel Dekker, Inc. publ., New York, 1982.

(53) Gross, J. L., Behrens, D. L., Mullins, D. E., Kornblith, P. L., and Dexter, D. L., Plasminogen activator and inhibitor activity in human glioma cells and modulation by sodium butyrate, Cancer Res. 48:291–296, 1988.

(54) Egholm, et al. Peptide Nucleic Acids (PNA)-Oligonucleotide Analogues with an Achiral Peptide Backbone, (1992)).

(55) Isacchi et al. 1990.

(56) Erolani et al., 1988.

(57) Van der krol, A. R. et al., Biotechniques 6(10):958–988, 1988.

---

What is claimed is:

1. An antisense oligomer of at least 20 nucleotides in length, which specifically binds to a portion of RNA expressed from the human fibroblast growth factor receptor type 1 (FGFR1) gene, alpha exon, wherein said oligomer is effective for reducing the expression of said FGFR1 gene.

2. The antisense oligomer of claim 1, said antisense oligomer having a sequence identified as SEQUENCE ID NO. 1.

3. The antisense oligomer of claim 1 wherein the nucleotides are selected from the group consisting of deoxyribonucleotides and ribonucleotides.

4. A composition comprising an antisense oligomer of at least 20 nucleotides in length, which specifically binds to a portion of RNA expressed from the human FGFR1 gene, alpha exon, wherein said oligomer is effective for reducing the expression of said FGFR1 gene, together with a pharmaceutically acceptable carrier.

5. The composition of claim 4 wherein said antisense oligomer has a sequence identified as SEQUENCE ID NO. 1.

6. The composition of claim 4 wherein the nucleotides are selected from the group consisting of deoxyribonucleotides and ribonucleotides.

* * * * *